US012605430B2

(12) United States Patent (10) Patent No.: US 12,605,430 B2
Wu et al. (45) Date of Patent: Apr. 21, 2026

(54) HIGH-ACTIVITY BLOOD COAGULATION FACTOR XI MUTANT Ala570Thr

(71) Applicants: RUIJIN HOSPITAL SHANGHAI JIAOTONG UNIVERSITY SCHOOL OF MEDICINE, Shanghai (CN); Wenman Wu, Shanghai (CN); Xuefeng Wang, Shanghai (CN); Qiulan Ding, Shanghai (CN)

(72) Inventors: Wenman Wu, Shanghai (CN); Xuefeng Wang, Shanghai (CN); Qiulan Ding, Shanghai (CN)

(73) Assignees: RUIJIN HOSPITAL SHANGHAI JIAOTONG UNIVERSITY SCHOOL OF MEDICINE, Shanghai (CN); Wenman Wu, Shanghai (CN); Xuefeng Wang, Shanghai (CN); Qiulan Ding, Shanghai (CN)

( * ) Notice: Subject to any disclaimer, the term of this patent is extended or adjusted under 35 U.S.C. 154(b) by 526 days.

(21) Appl. No.: 18/025,398

(22) PCT Filed: Apr. 13, 2021

(86) PCT No.: PCT/CN2021/086785

§ 371 (c)(1),
(2) Date: Mar. 9, 2023

(87) PCT Pub. No.: WO2022/052461

PCT Pub. Date: Mar. 17, 2022

(65) Prior Publication Data

US 2023/0338479 A1     Oct. 26, 2023

(30) Foreign Application Priority Data

Sep. 9, 2020    (CN) ........................ 202010941171.X

(51) Int. Cl.

| | |
|---|---|
| *C07K 14/745* | (2006.01) |
| *A61K 38/36* | (2006.01) |
| *A61K 38/39* | (2006.01) |
| *A61K 38/40* | (2006.01) |
| *A61K 38/48* | (2006.01) |
| *A61K 38/57* | (2006.01) |
| *A61K 48/00* | (2006.01) |
| *A61P 7/04* | (2006.01) |
| *C12N 9/64* | (2006.01) |

(52) U.S. Cl.

CPC .......... *A61K 38/4846* (2013.01); *A61K 38/39* (2013.01); *A61K 38/40* (2013.01); *A61K 38/57* (2013.01); *A61K 48/0066* (2013.01); *A61P 7/04* (2018.01); *C07K 14/745* (2013.01); *C12N 9/6443* (2013.01); *C12Y 304/21027* (2013.01)

(58) Field of Classification Search

CPC .. C07K 14/745; A61K 38/36; A61K 38/4846; A61K 38/39; A61K 38/40; C12N 9/6443; C12Y 304/21027; A61P 7/04

See application file for complete search history.

(56) References Cited

FOREIGN PATENT DOCUMENTS

| | | |
|---|---|---|
| CN | 102559720 | 7/2012 |
| CN | 108220274 | 6/2018 |
| CN | 112126636 | 12/2020 |
| EP | 1954822 | 8/2008 |

OTHER PUBLICATIONS

Bhattacharya et al. Impact of genetic variation on three dimensional structure and function of proteins. PLoS One 12(3): e0171355, 2017.*

Bork, P. Powers and pitfalls in sequence analysis: the 70% hurdle. Genome Res 10: 398-400, 2000.*

Bork, P. Go hunting in sequence databases but watch out for the traps. Trends in Genetics 12(10): 425-427, 1996.*

Brenner. S.E. Errors in genome annotation. Trends in Genetics 15:132-133, 1999.*

Definition of "gene" from Merriam-Webster Dictionary, www.merriam-webster.com/dictionary/gene; accessed Sep. 4, 2019.*

Doerks et al. Protein annotation: detective work for function prediction. Trends in Genetics 14:248-250, 1998.*

Fenton et al. Rheostat positions: a new classification of protein positions relevant to pharmacogenomics. Medicinal Chem Res 29: 1133-1146, 2020.*

Guo et al. Protein tolerance to random amino acid change. Proc Natl Acad Sci USA 101(25): 9205-9210, 2004.*

Harris et al. Analysis of 272 Genetic Variants in the Upgraded Interactive FXI Web Database Reveals New Insights into FXI Deficiency. TH Open 5: e543-e556, 2021.*

Lodish et al., Molecular Cell Biology. 4th edition. New York: W.H. Freeman; 2000. Section 9.1, Molecular Definition of a Gene.*

Skolnick et al. From genes to protein structure and function: novel applications of computational approaches in the genomic era. Trends Biotechnol 18(I):34-39 2000.*

Smith et al. The challenges of genome sequence annotation or "the devil is in the details". Nature Biotechnol 15: 1222-1223, 1997.*

Tischia et al. Factor XI gene variants in factor XI-deficient patients of Southern Italy: identification of a novel mutation and genotype-phenotype relationship. Human Genome Variation 4: 17043, 2017 (6 total pages).*

Tokuriki et al. Stability effects of mutations and protein evolvability. Curr Opin Structural Biol 19: 596-604, 2009.*

(Continued)

*Primary Examiner* — Bridget E Bunner

(74) *Attorney, Agent, or Firm* — JCIPRNET

(57) ABSTRACT

A high-activity blood coagulation factor XI mutant Ala570Thr (A570T), having nucleotide sequences as shown in SEQ ID NOs: 1-4 and an amino acid sequence as shown in SEQ ID NO: 5, is provided. The mutant is resistant to a physiological inhibitor thereof after being activated from a zymogen state to an active enzyme. Therefore, the mutant has a very high blood coagulation activity and a stronger catalytic ability for a non-physiological substrate; and the mutant is applied to the treatment of hemorrhagic diseases, and has good prospects in terms of gene therapy, gene editing and recombinant protein replacement treatments.

5 Claims, 15 Drawing Sheets

Specification includes a Sequence Listing.

(56) References Cited

OTHER PUBLICATIONS

Wiewel-Verschueren et al. Factor 11 single-nucleotide variants in women with heavy menstrual bleeding. J Obstet Gynaecol 37(7): 912-918, 2017.*

Wenman Wu; et al., "Factor XI Homodimer Structure Is Essential for Normal Proteolytic Activation by Factor XIIa, Thrombin, and Factor XIa," The Journal of Biological Chemistry, vol. 283, No. 27, Jul. 4, 2008, pp. 18655-18664.

Carfora V; et al., "coagulation factor XI isoform 1 preproprotein [*Homo sapiens*]," Genbank, NCBI Reference Sequence: NP_000119. 1, pp. 1-4, Dec. 27, 2022.

"International Search Report (Form PCT/ISA/210) of PCT/CN2021/ 086785," mailed on Jun. 10, 2021, with English translation thereof, pp. 1-8.

* cited by examiner

SEQ ID NO:1

```
1     atgatttttcttatatcaagtggtacatttcatttcatttacttcagtttctggtgaatgt   60
1      M  I  F  L  Y  Q  V  V  H  F  I  L  F  T  S  V  S  G  E  C     20
61    gtgactcagttgttgaaggacacctgctttgaaggagagggacattactacggtcttcaca   120
21     V  T  Q  L  L  K  D  T  C  F  E  G  G  D  I  T  T  V  F  T     40
121   ccaagcgccaagtactgccaggtagtctgcacttaccacccaagatgtttactcttcact   180
41     P  S  A  K  Y  C  Q  V  V  C  T  Y  H  P  R  C  L  F  T     60
181   ttcacggcggaatcaccatctgaggatcccacccgatggtttacttgtgtcctgaaagac   240
61     F  T  A  E  S  P  S  E  D  P  T  R  W  F  T  C  V  L  K  D    80
241   agtgttacagaaacactgccaagagtgaataggacagcagcgatttctgggtattctttc   300
81     S  V  T  E  T  L  P  R  V  N  R  T  A  A  I  S  G  Y  S  F    100
301   aagcaatgctcacaccaaataagcgcttgcaacaaagacatttatgtggacctagacatg   360
101    K  Q  C  S  H  Q  I  S  A  C  N  K  D  I  Y  V  D  L  D  M    120
361   aagggcataaactataaacagctcagttgccaagagtgctcaagaatgccaagaaagatgc   420
121    K  G  I  N  Y  N  S  S  V  A  K  S  A  Q  E  C  Q  E  R  C    140
421   acggatgacgtccactgccactttttcacgtacgccacaaggcagtttcccagcctggag   480
141    T  D  D  V  H  C  H  F  F  T  Y  A  T  R  Q  F  P  S  L  E    160
481   catcgtaacatttgtctactgaagcacacccaaacagggacaccaaccagaataacgaag   540
161    H  R  N  I  C  L  L  K  H  T  Q  T  G  T  P  T  R  I  T  K    180
541   ctcgataaagtggtgtctggattttcactgaaatcctgtgcacttttctaatctggcttgt   600
181    L  D  K  V  V  S  G  F  S  L  K  S  C  A  L  S  N  L  A  C    200
601   attagggacattttccctaatacggtgtgtttgcagacagcaacatcgacagtgtcatggct   660
201    I  R  D  I  F  P  N  T  V  F  A  D  S  N  I  D  S  V  M  A    220
661   ccgatgcttttgtctgtggccgaatctgcactcatcatcccggttgcttgttttttacc   720
221    P  D  A  F  V  C  G  R  I  C  T  H  H  P  G  C  L  F  F  T    240
721   ttcttttccaggaatggcccaaagaatctcaaagaaatctttgtctccttaaaacatct   780
241    F  F  S  Q  E  W  P  K  E  S  Q  R  N  L  C  L  L  K  T  S    260
781   gagagtggattgcccagtacacgcattaaaaagagcaaagctctttctggtttcagtcta   840
261    E  S  G  L  P  S  T  R  I  K  K  S  K  A  L  S  G  F  S  L    280
841   caaagctgccaggcacagcatcccagtgtttctgccattcttcattttaccatgacactgat   900
281    Q  S  C  R  H  S  I  P  V  F  C  H  S  S  F  Y  H  D  T  D    300
901   ttcttgggagaagaactggatattgttgctgcaaaaagtcacgaggcctgccagaaactg   960
301    F  L  G  E  E  L  D  I  V  A  A  K  S  H  E  A  C  Q  K  L    320
961   tgcaccaatgccgtccgctgccaattttttacttataccccagcccaagcatcctgcaac   1020
321    C  T  N  A  V  R  C  Q  F  F  T  Y  T  P  A  Q  A  S  C  N    340
1021  gaaggggaagggcaagtgttacttaaagcttctcttcaaacggatctccaactaaaatactt   1080
341    E  G  K  G  Q  V  L  K  L  S  S  N  G  S  F  T  K  I  L     360
1081  cacgggagaggaggcatctctggatacacattaaggttgtgtaaaatggataatgagtgt   1140
361    H  G  R  G  G  I  S  G  Y  T  L  R  L  C  K  M  D  N  E  C    380
1141  accaccaaaatcaagcccaggatcgttgaggaactgcgtctgttcgtggtgagtggccg   1200
381    T  T  K  I  K  P  R  I  V  G  G  T  A  S  V  R  G  E  W  P    400
1201  tggcaggtgacccgcacacaacctcacccactcagagacacctgtgtgggaggctccatc   1260
401    W  Q  V  T  L  H  T  T  S  P  T  Q  R  H  L  C  G  G  S  I    420
1261  attggaaaccagtggatattaacagccgctcactgtttctatgggtagagtcacctaag   1320
421    I  G  N  Q  W  I  L  T  A  A  H  C  F  Y  G  V  E  S  P  K    440
1321  atttgccgtgtctacagtggcattttaaatcaatctgaaataaaagaggacacatcttc   1380
441    I  L  R  V  Y  S  G  I  L  N  Q  S  E  I  K  E  D  T  S  F    460
1381  tttggggttcaagaaataataatccatgatcagtataaaatggcagaaagcgggtatgat   1440
461    F  G  V  Q  E  I  I  I  H  D  Q  Y  K  M  A  E  S  G  Y  D    480
1441  attgccttgttgaaactggaaaccacagtgaattacacagattctcaacgacccatatgc   1500
481    I  A  L  L  K  L  E  T  T  V  N  Y  T  D  S  Q  R  P  I  C    500
1501  ctgccttccaaaggagatagaaatgtaatatacactgattgctgggtgactggatggggg   1560
500    L  P  S  K  G  D  R  N  V  I  Y  T  D  C  W  V  T  G  W  G    520
1561  tacagaaaactaagagacaaaatacaaaatactctccagaaagccaagataccttagtg   1620
521    Y  R  K  L  R  D  K  I  Q  N  T  L  Q  K  A  K  I  P  L  V    540
1621  accacgaagatgccagaagagatacagaggacataaaaataacccataagatgatctgt   1680
541    T  N  E  C  Q  K  R  Y  R  G  H  K  I  T  H  K  M  I  C    560
1681  gccggctacagggaaggaggaggaaggacacttgcaagggagattcgggaggcctctgtcc   1740
561    A  G  Y  R  E  G  G  K  D  T  C  K  G  D  S  G  G  P  L  S    580
1741  tgcaaacacaatgaggtctggcatctggtagccatcacgagctgggcgaaggctgtgct   1800
581    C  K  H  N  E  V  W  H  L  V  G  I  T  S  W  G  E  G  C  A    600
1801  caaagggagcggccaggtgtttacaccaacgtggtcgagtacgtggactggattctggag   1860
600    Q  R  E  R  P  G  V  Y  T  N  V  V  E  Y  V  D  W  I  L  E    620
1861  aaaactcaagcagtgtga   1878
621    K  T  Q  A  V  -   626
```

FIG. 1

SEQ ID NO:2

```
1      atgattttcttatatcaagtggtacatttcatttatttacttcagtttctggtgaatgt      60
1        M  I  F  L  Y  Q  V  V  H  F  I  L  F  T  S  V  S  G  E  C      20
61     gtgactcagttgttgaaggacacctgctttgaaggaggggacattactacggtcttcaca     120
21       V  T  Q  L  L  K  D  T  C  F  E  G  G  D  I  T  T  V  F  T      40
121    ccaagcgccaagtactgccaggtagtctgcacttaccacccaagatgtttactcttcact     180
41       F  S  A  K  Y  C  Q  V  V  C  T  Y  H  P  R  C  L  L  F  T      60
181    ttcacggcggaatcaccatctgaggaccccgatggttcacttgtgtcctgaaagac        240
61       F  T  A  E  S  P  S  E  D  P  T  R  W  F  T  C  V  L  K  D      80
241    agtgttacagaaacactgccaagagtgaataggacagcagcgatttctgggtattctttc     300
81       S  V  T  E  T  L  P  R  V  N  R  T  A  A  I  S  G  Y  S  F     100
301    aagcaatgctcacaccaaataagcgcttgcaacaaagacatttatgtggacctagacatg     360
101      K  Q  C  S  H  Q  I  S  A  C  N  K  D  I  Y  V  D  L  D  M     120
361    aagggcataaactataacagctcagttgccaagagtgctcaagaatgccagaaagatgc     420
121      K  G  I  N  Y  N  S  S  V  A  K  S  A  Q  E  C  Q  E  R  C     140
421    acggatgacgtccactgccacttttttcacgtacgccacaaggcagtttcccagcctggag    480
141      T  D  D  V  H  C  H  F  F  T  Y  A  T  R  Q  F  P  S  L  E     160
481    catcgtaacatttgtctactgaagcacccaaacagggacaccagaataacgaag          540
161      H  R  N  I  C  L  L  K  H  T  Q  T  G  T  P  T  R  I  T  K     180
541    ctcgataaagtggtgtctggattttcactgaaatcctgtgcactttctaatctggcttgt    600
181      L  D  K  V  V  S  G  F  S  L  K  S  C  A  L  S  N  L  A  C     200
601    attaggacattttccctaatacggtgtttgcagacagcaacatcgacagtgtcatggct     660
201      I  R  D  I  F  P  N  T  V  F  A  D  S  N  I  D  S  V  M  A     220
661    cccgatgcttttgtctgtggccgaatctgcactcatcatcccggttgcttgttttttacc    720
221      P  D  A  F  V  C  G  R  I  C  T  H  H  P  G  C  L  F  F  T     240
721    ttcttttcccaggaatggcccaaagaatctcaaagaaatctttgtctccttaaaacatct    780
241      F  F  S  Q  E  W  P  K  E  S  Q  R  N  L  C  L  L  K  T  S     260
781    gagagtggattgcccagtacacgcattaaaagagcaaagtctttctggtttcagtcta      840
261      E  S  G  L  P  S  T  R  I  K  K  S  K  A  L  G  F  S  L        280
841    caaagctgcaggcacagcatcccagtgttctgccattcttcattttaccatgacactgat    900
281      Q  S  C  R  H  S  I  P  V  F  C  H  S  S  F  Y  H  D  T  D     300
901    ttcttgggagaagaactggatattgttgctgcaaaaagtcacgaggcctgccagaaactg    960
301      F  L  G  E  E  L  D  I  V  A  A  K  S  H  E  A  C  Q  K  L     320
961    tgcaccaatgccgtccgctgccagttttttacctataccccagcccagcatcctgcaac    1020
321      C  T  N  A  V  R  C  Q  F  F  T  Y  T  P  A  Q  A  S  C  N     340
1021   gaagggaagggcaagtgttacttaaagctttcttcaaacggatctccaactaaaatactt   1080
341      E  G  K  G  K  C  Y  L  K  L  S  S  N  G  S  P  T  K  I  L     360
1081   cacgggagaggaggcatctctggatacacattaaggttgtgtaaaatggataatgagtgt   1140
361      H  G  R  G  G  I  S  G  Y  T  L  R  L  C  K  M  D  N  E  C     380
1141   accaccaaaatcaagcccaggatcgttggaggaactgcgtctgttcgtggtgagtggccg   1200
381      T  T  K  I  K  P  R  I  V  G  G  T  A  S  V  R  G  E  W  P     400
1201   tggcaggtgaccctgcacacaacctcacccactcagagacacctgtgtggaggctccatc   1260
401      W  Q  V  T  L  H  T  T  S  P  T  Q  R  H  L  C  G  G  S  I     420
1261   attggaaaccagtggatattaacagccgctcactgtttctatggggtagagtcacctaag   1320
421      I  G  N  Q  W  I  L  T  A  A  H  C  F  Y  G  V  E  S  P  K     440
1321   attttgcgtgtctacagtggcattttaaatcaatctgaaataaaagaggacacatcttc    1380
441      I  L  R  V  Y  S  G  I  L  N  Q  S  E  I  K  E  D  T  S  F     460
1381   tttgggggttcaagaataataatccatgatcagtataaaatggcagaaagcgggtatgat   1440
461      F  G  V  Q  E  I  I  I  H  D  Q  Y  K  M  A  E  S  G  Y  D     480
1441   attgccttgttgaaactggaaaccacagtgaattacacagattctcaacgaccatatgc    1500
481      I  A  L  L  K  L  E  T  T  V  N  Y  T  D  S  Q  R  P  I  C     500
1501   ctgccttccaaggagatagaaatgtaatatacactgattgctgggtgactggatggggg    1560
500      L  P  S  K  G  D  R  N  V  I  Y  T  D  C  W  V  T  G  W  G     520
1561   tacagaaaactaagagacaaaatacaaaatactctccagaaagccaagataccttagtg    1620
521      Y  R  K  L  R  D  K  I  Q  N  T  L  Q  K  A  K  I  P  L  V     540
1621   accaacgaagagtgccagaagagatacagaggacataaaataaccataagatgatctgt    1680
541      T  N  E  E  C  Q  K  R  Y  R  G  H  K  I  T  H  K  M  I  C     560
1681   gccggctacaggaaggaggagggaaggacaᴛctgcaaggggagattcgggaggccctctgtcc  1740
561      A  G  Y  R  E  G  G  K  D  T  C  K  G  D  S  G  G  P  L  S     580
1741   tgcaaacacaatgaggtctggcatctggtaggcatcacgagctggggggaaggctgtgct   1800
581      C  K  H  N  E  V  W  H  L  V  G  I  T  S  W  G  E  G  C  A     600
1801   caaagggagcggccaggtgtttacaccaacgtggtcgagtacgtggactggattctggag   1860
600      Q  R  E  R  P  G  V  Y  T  N  V  V  E  Y  V  D  W  I  L  E     620
1861   aaaactcaagcagtgtga                                             1878
621      K  T  Q  A  V  -                                             626
```

FIG. 2

SEQ ID NO:3

```
1     atgattttcttatatcaagtggtacatttcattttatttacttcagtttctggtgaatgt    60
1     M  I  F  L  Y  Q  V  V  H  F  I  L  F  T  S  V  S  G  E  C     20
61    gtgactcagttgttgaaggacacctgctttgaaggaggggacattactacggtcttcaca   120
21    V  T  Q  L  L  K  D  T  C  F  E  G  G  D  I  T  T  V  F  T     40
121   ccaagcgccaagtactgccaggtagtctgcacttaccaccccaagatgtttactcttcact  180
41    P  S  A  K  Y  C  Q  V  V  C  T  Y  H  P  K  C  L  L  F  T     60
181   ttcacggcggaatcaccatcggagatcccacccgatggtttacttgtgtcctgaaagac   240
61    F  T  A  E  S  P  S  E  D  P  T  R  W  F  T  C  V  L  K  D     80
241   agtgttacagaaacactgccaagagtgaataggacagcagcgatttctgggtattctttc   300
81    S  V  T  E  T  L  P  R  V  N  R  T  A  A  I  S  G  Y  S  F     100
301   aagcaatgctcacaccaaataagcgcttgcaacaaagacatttatgtggacctagacatg   360
101   K  Q  C  S  H  Q  I  S  A  C  N  K  D  I  Y  V  D  L  D  M     120
361   aagggcataaactataacagctcagttgccaagagtgctcaagaatgccagaaagatgc   420
121   K  G  I  N  Y  N  S  S  V  A  K  S  A  Q  E  C  Q  E  R  C     140
421   acggatgacgtccactgccactttttcacgtacgccacaaggcagtttccagcctggag   480
141   T  D  D  V  H  C  H  F  F  T  Y  A  T  R  Q  F  P  S  L  E     160
481   catcgtaacatttgtctactgaagcacacccagggaccaaccagaataacgaag   540
161   H  R  N  I  C  L  L  K  H  T  Q  T  G  T  P  T  R  I  T  K     180
541   ctcgataaagtggtgtctggattttcactgaaatcctgtgcactttctaatctggcttgt   600
181   L  D  K  V  V  S  G  F  S  L  K  S  C  A  L  S  N  L  A  C     200
601   attagggacatttttcctaatacggtgtttgcagacagcaacatcgacagtgtcatggct   660
201   I  R  D  I  F  P  N  T  V  F  A  D  S  N  I  D  S  V  M  A     220
661   cccgatgcttttgtctgtggccgaatctgcactcatcatcccggttgcttgttttttacc   720
221   P  D  A  F  V  C  G  R  I  C  T  H  H  P  G  C  L  F  F  T     240
721   ttcttttccaggaatggcccaaagaatctcaaagaaatctttgtctcttaaaacatct   780
241   F  F  S  Q  E  W  P  K  E  S  Q  R  N  L  C  L  L  K  T  S     260
781   gagagtggattgcccagtacacgcattaaaaagagcaaagctcttctggtttcagtcta   840
261   E  S  G  L  P  S  T  R  I  K  K  S  K  A  L  S  G  F  S  L     280
841   caaagctgcaggcacagcatccagtgttctgccattcttcattttaccatgacactgat   900
281   Q  S  C  R  H  S  I  P  V  F  C  H  S  F  Y  H  D  T  D     300
901   ttcttgggagaagaactggatattgttgctgcaaaaagtcacgaggcctgccagaaactg   960
301   F  L  G  E  E  L  D  I  V  A  A  K  S  H  E  A  C  Q  K  L     320
961   tgcaccaatgccgtccgctgccagttttttacctataccccagcccaagcatcctgcaac   1020
321   C  T  N  A  V  R  C  Q  F  F  T  Y  T  P  A  Q  A  S  C  N     340
1021  gaagggaagggcaagtgttacttaaagctttcttcaaacggatctccaactaaaatactt   1080
341   E  G  K  G  K  C  Y  L  K  L  S  S  N  G  S  P  T  K  I  L     360
1081  cacggagaggaggcatctctggatacacattaaggttgtgtaaaatggataatgagtgt   1140
361   H  G  R  G  G  I  S  G  Y  T  L  R  L  C  K  M  D  N  E  C     380
1141  accaccaaaatcaagccaggatcgttggaggaactgcgtctgttcgttggtgagtggccg   1200
381   T  T  K  I  K  P  R  I  V  G  G  T  A  S  V  R  G  E  W  P     400
1201  tggcaggtgaccctgcacacaacctcacccactcagagacacctgtgtggaggctccatc   1260
401   W  Q  V  T  L  H  T  T  S  P  T  Q  R  H  L  C  G  G  S  I     420
1261  attggaaaccagtggatattaacagccgctcactgtttctatggggtagagtcacctaag   1320
421   I  G  N  Q  W  I  L  T  A  A  H  C  F  Y  G  V  E  S  P  K     440
1321  attttgcgtgtctacagtggcattttaaatcaatctgaaataaaagaggacacatctttc   1380
441   I  L  R  V  Y  S  G  I  L  N  Q  S  E  I  K  E  D  T  S  F     460
1381  tttggggttcaagaaataataatccatgatcagtataaaatggcagaaagcgggtatgat   1440
461   F  G  V  Q  E  I  I  I  H  D  Q  Y  K  M  A  E  S  G  Y  D     480
1441  attgccttgttgaaactggaaccacagtgaattacacagattctcaacgacccatatgc   1500
481   I  A  L  L  K  L  E  T  T  V  N  Y  T  D  S  Q  R  P  I  C     500
1501  ctgccttccaaaggagataaaatgtaatatacactgattgctggtgactggatggggg   1560
500   L  P  S  K  G  D  R  N  V  I  Y  T  D  C  W  V  T  G  W  G     520
1561  tacagaaaactaagagacaaaatacaaatactctccagaaagccaagataccttagtg   1620
521   Y  R  K  L  R  D  K  I  Q  N  T  L  Q  K  A  K  I  P  L  V     540
1621  accaacgaagagtgccagaagagatacagaggacataaaataacccataagatgatctgt   1680
541   T  N  E  C  Q  K  R  Y  R  G  H  K  I  T  H  K  M  I  C     560
1681  gccggctacagggaaggaggaggaaggacacgtgcaagggagattcgggaggccctctgtcc   1740
561   A  G  Y  R  E  G  G  K  D  T  C  K  G  D  S  G  G  P  L  S     580
1741  tgcaaacacaatgaggtctggcatctggtaggcatcacgagctggggcgaaggctgtgct   1800
581   C  K  H  N  E  V  W  H  L  V  G  I  T  S  W  G  E  G  C  A     600
1801  caaaggggagcggaggtgtttacaccaacgtggtcgagtacgtggactggattctggag   1860
600   Q  R  E  R  P  G  V  Y  T  N  V  V  E  Y  V  D  W  I  L  E     620
1861  aaaactcaagcagtgtga                                              1878
621   K  T  Q  A  V  -                                                626
```

FIG. 3

SEQ ID NO:4

```
1      atgattttcttatatcaagtggtacattcattttatttacttcagtttctggtgaatgt   60
1       M  I  F  L  Y  Q  V  V  H  F  I  L  F  T  S  V  S  G  E  C    20
61     gtgactcagttgttgaaggacacctgctttgaaggagggacattactacggtcttcaca  120
21      V  T  Q  L  L  K  D  T  C  F  E  G  G  D  I  T  T  V  F  T    40
121    ccaagcgccaagtactgccaggtagtctgcacttaccacccaagatgtttactcttcact  180
41      P  S  A  K  Y  C  Q  V  V  C  T  Y  H  P  R  C  L  L  F  T    60
181    ttcacggcggaatcaccatcgaggatcccaccgatggttttacttgtgtcctgaaagac  240
61      F  T  A  E  S  P  S  E  D  P  T  R  W  F  T  C  V  L  K  D    80
241    agtgttacagaaacactgccaagagtgaataggacagcagcgatttctgggtattctttc  300
81      S  V  T  E  T  L  P  R  V  N  R  T  A  A  I  S  G  Y  S  F   100
301    aagcaatgctcacaccaaataagccgcttgcaacaaagacatttatgtggacctagacatg  360
101     K  Q  C  S  H  Q  I  S  A  C  N  K  D  I  Y  V  D  L  D  M   120
361    aagggcataaactataacagctcagttgccaagagtgctcaagaatgccaagaagatgc  420
121     K  G  I  N  Y  N  S  S  V  A  K  S  A  Q  E  C  Q  E  C     140
421    acggatgacgtccactgccactttttcacgtacgccacaaggcagtttccagcctggag  480
141     T  D  D  V  H  C  F  F  T  Y  A  T  R  Q  F  P  S  L  E      160
481    catcgtaacatttgtctactgaagcacacccaaacagggacaccaaccagaataacgaag  540
161     H  R  N  I  C  L  L  K  H  T  Q  T  G  T  P  T  R  I  T  K   180
541    ctcgataaagtggtgtctggattttcactgaaatcctgtgcactttctaatctggcttgt  600
181     L  D  K  V  V  S  G  F  S  L  K  S  C  A  L  S  N  L  A  C   200
601    attagggacattttccctaatacggtgtttgcagacagcaacatcgacagtgtcatggct  660
201     I  R  D  I  F  P  N  T  V  F  A  D  S  N  I  D  S  V  M  A   220
661    cccgatgcttttgtctgtggccgaatctgcactcatcatcccggttgcttgtttttacc  720
221     P  D  A  F  V  C  G  R  I  C  T  H  H  P  G  C  L  F  F  T   240
721    ttcttttccaggaatggcccaaagaatctcaaagaaatctttgtctccttaaaacatct  780
241     F  F  S  Q  E  W  P  K  E  S  Q  R  N  L  C  L  L  K  T  S   260
761    gagagtggattgcccagtacacgcattaaaaagagcaaagctctttctggttttcagtcta  840
261     E  S  G  L  P  S  T  R  I  K  K  S  K  A  L  S  G  F  S  L   280
841    caaagctgcaggcacagcatccagtgttctgccattcttcattttaccatgacactgat  900
281     Q  S  C  R  H  S  I  F  V  F  H  S  S  F  Y  H  D  T  D     300
901    ttcttgggagaagaactggatattgttgctgcaaaaagtcacgaggctgccagaaactg  960
301     F  L  G  E  E  L  D  I  V  A  A  K  S  H  E  A  Q  K  L     320
961    tgcaccaatgccgtccgctgccagttttttacctatacccagcccaagcatcctgcaac 1020
321     C  T  N  A  V  R  C  Q  F  F  T  Y  P  A  Q  A  S  N       340
1021   gaaggggaagggcaagtgttacttaaagctttcttcaaacggatctccaactaaaatactt 1080
341     E  G  K  G  K  C  Y  L  K  L  S  S  N  G  S  P  T  K  I  L  360
1081   cacgggagaggaggcatctctggatacacattaaggttgtgtaaaatggataatgagtgt 1140
361     H  G  R  G  G  I  S  G  Y  T  L  R  L  C  K  M  D  N  E  C  380
1141   accaccaaaatcaagcccaggatcgttggaggaactgcgtctgttcgtggtgagtggccg 1200
381     T  T  K  I  K  P  R  I  V  G  G  T  A  S  V  R  G  E  W  P  400
1201   tggcaggtgaccctgcacacaacctcacccactcagagacaccgtgtgtggaggctccatc 1260
401     W  Q  V  T  L  H  T  T  S  P  T  Q  R  H  L  C  G  G  S  I  420
1261   attggaaaccagtggatattaacagccgctcactgtttctatgggggtagagtcacctaag 1320
421     I  G  N  Q  W  I  L  T  A  A  H  C  F  Y  G  V  E  S  P  K  440
1321   attttggcgtgtctacagtggcattttaaatcaatctgaaataaaagaggacacatctttc 1380
441     I  L  R  V  Y  S  G  I  L  N  Q  S  E  I  K  E  D  T  S  F  460
1381   tttggggttcaagaataataatccatgatcagtataaaatggcagaaagcgggtatgat 1440
461     F  G  V  Q  E  I  I  I  H  D  Q  Y  K  M  A  E  S  G  Y  D  480
1441   attgccttgttgaaactggaaaccacagtgaattacacagattctcaacgacccatatgc 1500
491     I  A  L  L  K  L  E  T  T  V  N  Y  T  D  S  Q  R  P  I  C  500
1501   ctgccttccaaaggagatagaaatgtaatatacactgattgctgggtgactggatggggg 1560
500     L  P  S  K  G  D  R  N  V  I  Y  T  D  C  W  V  T  G  W  G  520
1561   tacagaaaactaagagacaaaatacaaaatactctccagaaagccaagataccttagtg 1620
521     Y  R  K  L  R  D  K  I  Q  N  T  L  Q  K  A  K  I  P  L  V  540
1621   accacagaagtgccaaaagagatacagaggacataaaaccatcaagatgatctgt 1680
541     T  N  E  Q  K  R  Y  R  G  H  K  I  T  H  K  M  I  C       560
1681   gccggctacagggaaggagggaaggacactgcaagggagattcgggaggccctctgtcc 1740
561     A  G  Y  R  E  G  G  K  D  T  C  K  G  D  S  G  G  P  L  S  580
1741   tgcaaacacaatgaggtctggcatctgttaggcatcacgagctggggcgaaggctgtgct 1800
581     C  K  H  N  E  V  W  H  L  V  G  I  T  S  W  G  E  C  A     600
1801   caaagggagcggccaggtgtttacaccaacgtggtcgagtacgtggactggattctggag 1860
600     Q  R  E  P  G  V  Y  T  N  V  V  E  Y  V  D  W  I  L  E     620
1861   aaaactcaagcagtgtga 1878
621     K  T  Q  A  V  - 626
```

FIG. 4

SEQ ID NO:5

MIFLYQVVHFILFTSVSGECVTQLLKDTCFEGGDITTVFTPSAKYCQVVCTYHPRCLLFTFTAESPSEDPTRWFTC
VLKDSVTETLPRVNRTAAISGYSFKQCSHQISACNKDIYVDLDMKGINYNSSVAKSAQECQERCTDDVHCHFFTYA
TRQFPSLEHRNICLLKHTQTGTPTRITKLDKVVSGFSLKSCALSNLACIRDIFPNTVFADSNIDSVMAPDAFVCGR
ICTHHPGCLFFTFFSQEWPKESQRNLCLLKTSESGLPSTRIKKSKALSGFSLQSCRHSIPVFCHSSFYHDTDFLGE
ELDIVAAKSHEACQKLCTNAVRCQFFTYTPAQASCNEGKGKCYLKLSSNGSPTKILHGRGGISGYTLRLCKMDNEC
TTKIKPRIVGGTASVRGEWPWQVTLHTTSPTQRHLCGGSIIGNQWILTAAHCFYGVESPKILRVYSGILNQSEIKE
DTSFFGVQEIIIHDQYKMAESGYDIALLKLETTVNYTDSQRPICLPSKGDRNVIYTDCWVTGWGYRELRDKIQNTL
QKAKIPLVTNEECQKRYRGHKITHKMICAGYREGGKDTCKGDSGGPLSCKHNEVWHLVGITSWGEᴛᴄᴀDRERPGVY
TNVVEYVDWILEKTQAV-

FIG. 5

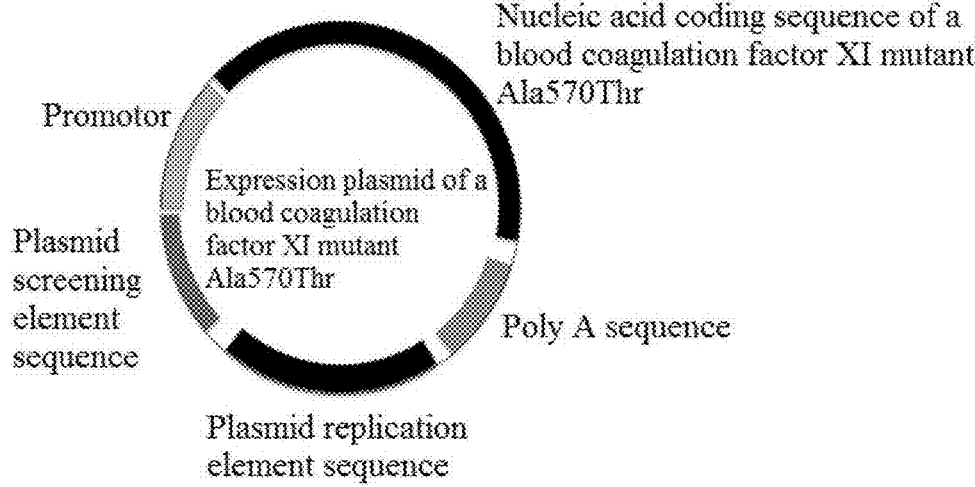

FIG. 6

Blood coagulation factor VIII inhibitor+buffer control

Blood coagulation factor VIII inhibitor+blood coagulation factor XI mutant Ala570Thr of a 1/8 physiological concentration Blood coagulation factor VIII inhibitor | blood coagulation factor XI mutant Ala570Thr of a 1/2 physiological concentration Blood coagulation factor VIII inhibitor+blood coagulation factor XI mutant Ala570Thr of the physiological concentration

HIGH-ACTIVITY BLOOD COAGULATION FACTOR XI MUTANT Ala570Thr

CROSS-REFERENCE TO RELATED APPLICATION

This is a 371 application of the International PCT application serial no. PCT/CN2021/086785, filed on Apr. 13, 2021, which claims the priority benefits of China Application No. 202010941171.X, filed on Sep. 9, 2020. The entirety of each of the above-mentioned patent applications is hereby incorporated by reference herein and made a part of this specification.

REFERENCE TO A SEQUENCE LISTING

The instant application contains a Sequencing Listing which has been submitted electronically in ASCII text file and is hereby incorporated by reference in its entirety. Said ASCII copy, created on Jan. 8, 2026, is named 131867-US-Sequence Listing and is 16,258 bytes in size.

TECHNICAL FIELD

The present invention belongs to the field of hemorrhagic disease treatment, and specifically relates to a high-activity blood coagulation factor XI mutant Ala570Thr.

DESCRIPTION OF RELATED ART

Hemorrhagic diseases can be caused by blood coagulation factor deficiency or other coagulation disorders in the human body. The hemorrhagic diseases caused by blood coagulation factor VIII/IX (FVIII/FIX) deficiency are called hemophilia (A/B). In severe patients, the activity of blood coagulation factors VIII/IX is often less than 1% of a normal level, and spontaneous hemorrhage often occurs, leading to muscle hematoma or joint deformity. Supplementing the level of blood coagulation factors VIII/IX in patients by infusion of a factor VIII/IX preparation (currently usually recombinant expressed coagulation factor VIII/IX protein in vitro) is currently the only effective treatment method, but it requires frequent dosing. Gene therapy is currently a treatment method in clinical trials, which introduces the normal blood coagulation factor VIII/IX gene into patients for expression, so as to achieve the purposes of improving the level of coagulation factors VIII/IX and preventing bleeding. Although hemophilia A and B can be effectively treated with recombinant or plasma-derived FVIII/FIX, an antibody is produced in about 30% of patients after treatment, which makes the treatment ineffective. Bypass coagulant active drugs are the best choice to treat hemophilia patients with inhibitors. However, the currently clinically used blood coagulation factor VIIa (FVIIa) has a short half-life (about 2 hours), a large dosage (90-100 μg/kg body weight) and high treatment cost. Therefore, how to obtain a new bypass coagulation pathway drug with better therapeutic effects and drug metabolism characteristics is an urgent problem to be solved in the treatment of hemophilia at present.

A blood coagulation factor IX is a physiological substrate of a blood coagulation factor XI (FXI), and the coagulation activity of the blood coagulation factor XI is mainly related to its ability to efficiently cleave and activate the blood coagulation factor IX. However, other components in a coagulation reaction may also be catalytically cleaved by the coagulation factor XI. Recent studies have shown that the blood coagulation factor XI can catalyze the activation of a blood coagulation factor V (FV) and a blood coagulation factor X (FX), thus directly activating a common pathway of coagulation over the coagulation factor IX; another study also shows that the blood coagulation factor XI can degrade a tissue factor pathway inhibitor (TFPI), thus prolonging the action time of an exogenous pathway-activated blood coagulation factor FVII (FVIIa) and indirectly amplifying the exogenous pathway-activated coagulation reaction. However, the efficiency of the wild-type blood coagulation factor XI to catalytically cleave bypass coagulation reaction substrates including FX, FV or TFPI is very low, which limits its ability to promote the coagulation reaction through bypass.

SUMMARY

The technical problem to be solved by the present invention is to provide a high-activity blood coagulation factor XI mutant Ala570Thr (A570T), and the mutant is resistant to a physiological inhibitor thereof after being activated from a zymogen state to an active enzyme. Therefore, the mutant has a very high blood coagulation activity and a stronger catalytic ability for a non-physiological substrate; and the mutant is applied to the treatment of hemorrhagic diseases, and has good prospects in terms of gene therapy, gene editing and recombinant protein replacement treatments.

The present invention provides a high-activity blood coagulation factor XI mutant Ala570Thr, having
- (1) a nucleotide sequence as shown in SEQ ID NO: 1; or
- (2) a nucleotide sequence as shown in SEQ ID NO: 2; or
- (3) a nucleotide sequence as shown in SEQ ID NO: 3; or
- (4) a nucleotide sequence as shown in SEQ ID NO: 4; or
    a combination of mutations of any other nucleotide at positions 1708, 1709 and 1710.

The present invention also provides a mutein of a high-activity blood coagulation factor XI mutant Ala570Thr, wherein an amino acid sequence is as shown in SEQ ID NO: 5, and an amino acid, located at position 570, of the mutant is Thr (denoted as Ala570Thr) rather than Ala of non-human wild-type FXI (hFXI); or any other amino acid mutates at the position.

The present invention also provides a nucleic acid encoding a mutein of a high-activity blood coagulation factor XI mutant Ala570Thr, or a nucleic acid having the same length as the coding nucleic acid and being completely complementary to the coding nucleic acid.

The present invention also provides a vector expressing a mutein of a high-activity blood coagulation factor XI mutant Ala570Thr.

The present invention also provides a method for preparing a mutein of a high-activity blood coagulation factor XI mutant Ala570Thr, including the following steps:
- (1) ligating a gene encoding the high-activity blood coagulation factor XI mutant Ala570Thr into a vector to obtain a recombinant vector;
- (2) transforming the recombinant vector described above into a host cell to obtain clones of mutant cells expressing a recombinant coagulation factor XI Ala570Thr;
- (3) performing continuous perfusion culture on the recombinant cell clones in a serum-free medium to induce expression of the mutein of the recombinant coagulation factor XI Ala570Thr; and
- (4) separating, purifying, filtering, finally filling, and freeze-drying to obtain the expressed high-activity blood coagulation factor XI Ala570Thr mutein.

The serum-free medium in the step (3) is "SAFC Biosciences EX-CELL™ 302" (a commercial reagent).

The purifying in the step (4) includes primary purifying and refined purifying.

The present invention also provides a plasmid vector expressing a mutein Ala570Thr for gene transduction, and the preparation and testing of the plasmid vector includes the following step: ligating cDNA encoding the high-activity blood coagulation factor XI mutant Ala570Thr into a gene expression plasmid containing CMV or other eukaryotic cell expression promoters (with or without liver tissue specificity).

The mutein of the high-activity blood coagulation factor XI mutant Ala570Thr is applied to the preparation of gene therapy drugs.

The mutein of the high-activity blood coagulation factor XI mutant Ala570Thr is applied to the preparation of recombinant protein therapeutic drugs for hemophilia or other hemorrhagic diseases.

The mutein of the high-activity blood coagulation factor XI mutant Ala570Thr is applied to the preparation of a fusion protein of the blood coagulation factor XI mutant Ala570Thr, which is applied to recombinant protein therapeutic drugs for hemophilia or other hemorrhagic diseases.

The fusion protein is human albumin, immunoglobulin Fc, transferrin or alpha 1 antitrypsin.

A pharmaceutical composition or gene therapy vector of the nucleic acid or amino acid sequence of the present invention is used for preventing and/or treating diseases, wherein the diseases mainly include hemorrhagic diseases or bleeding caused by various reasons; and the most likely hemorrhagic diseases are hemophilia A and B, that is, hemorrhagic diseases caused by hereditary blood coagulation factor VIII or IX deficiency, and include hemophilia A and B in which inhibitory antibody production is present, or acquired blood coagulation factor VIII or IX deficiency caused by inhibitor production; and other hemorrhagic diseases using bypass preparations, such as neonatal coagulation disorders; severe liver disease; high-risk surgery; traumatic blood loss; bone marrow transplantation; thrombocytopenia and platelet dysfunction; emergency reversal of oral anticoagulants; congenital defects of coagulation factors V, VII, X and XI; von Willebrand disease, and acquired von Willebrand disease caused by von Willebrand factor inhibitors, blood loss associated with massive injury, cerebral hemorrhage and platelet dysfunction.

Beneficial Effects

Unlike the mechanism of improving the coagulation activity of the blood coagulation factor XI, which is mainly based on acceleration of the conversion of a blood coagulation factor XI mutant Gly397Ser from zymogen to an enzyme with the catalytic activity, the blood coagulation factor XI mutant Ala570Thr in the present invention is resistant to a physiological inhibitor thereof (such as protein nexin II/KPI) after being activated from a zymogen state to an active enzyme (activated blood coagulation factor XI, FXIa). Therefore, the mutant has a very high blood coagulation activity and a stronger catalytic ability for a non-physiological substrate, thus enhancing the blood coagulation activity of a bypass pathway, activating the coagulation reaction efficiently by the bypass pathway through a mechanism independent of a blood coagulation factor IX (FIX)/a blood coagulation factor VIII (FVIII), improving the overall blood coagulation function of the body, and being applied to the treatment of hemorrhagic diseases, and has good prospects in terms of gene therapy and recombinant protein replacement treatments.

BRIEF DESCRIPTION OF THE DRAWINGS

FIGS. 1-5 are schematic diagrams showing the sequences of the nucleic acid and encoded protein of a high-activity blood coagulation factor XI mutant Ala570Thr (i.e., A570T) of the present invention;

FIG. 6 is a schematic diagram showing a structure of a vector of the present invention;

FIG. 9a to FIG. 9h are schematic diagrams of thromboelastogram for detecting correction of coagulation defects in acquired hemophilia with antibodies against the coagulation factor VIII by the blood coagulation factor XI mutant Ala570Thr; wherein, FIG. 9a is a blood coagulation factor VIII+buffer control, FIG. 9b is a blood coagulation factor VIII inhibitor+blood coagulation factor XI mutant Ala570Thr of a ⅛ physiological concentration, FIG. 9c is a blood coagulation factor VIII inhibitor+blood coagulation factor XI mutant Ala570Thr of a ¼ physiological concentration, FIG. 9d is a blood coagulation factor VIII inhibitor+blood coagulation factor XI mutant Ala570Thr of a ½ physiological concentration, FIG. 9e is a blood coagulation factor VIII inhibitor+blood coagulation factor XI mutant Ala570Thr of the physiological concentration, FIG. 9f is a blood coagulation factor VIII inhibitor+blood coagulation factor XI mutant Ala570Thr of 2 times physiological concentration, FIG. 9g is a blood coagulation factor VIII deficiency+buffer control, and FIG. 9h is a blood coagulation factor VIII deficiency+blood coagulation factor XI mutant Ala570Thr of the physiological concentration.

DESCRIPTION OF THE EMBODIMENTS

Figure 7:
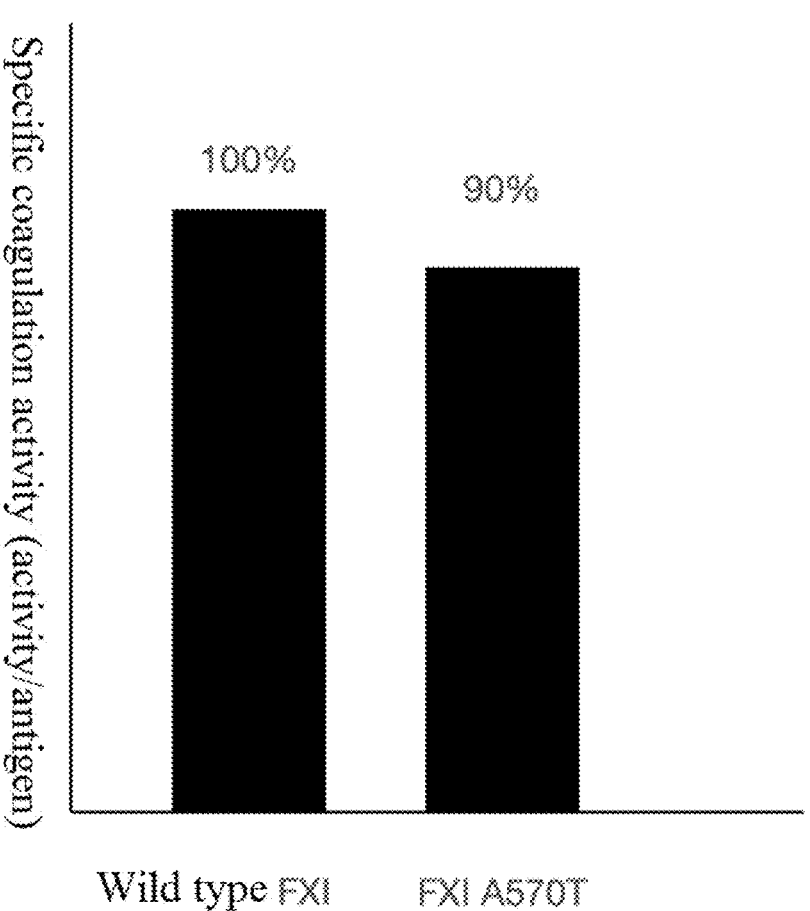
FIG. 7 is a schematic diagram showing the activity of the high-activity blood coagulation factor XI mutant Ala570Thr of the present invention.

The present invention will be further described below in connection with specific embodiments. It should be understood that these embodiments are only intended to illustrate the present invention and are not intended to limit the scope of the present invention. In addition, it should be understood that after reading the contents of the present invention as taught, those skilled in the art may make various changes or modifications to the present invention, and these equivalent forms also fall within the scope defined by the appended claims of this application.

Embodiment 1

An amino acid sequence of a mutein of a high-activity blood coagulation factor XI mutant Ala570Thr is shown in SEQ ID NO: 5.

A preparation method of the mutein of the high-activity blood coagulation factor XI mutant Ala570Thr includes the following steps:

(1) ligating a gene encoding a human wild-type coagulation factor XI or the blood coagulation factor XI mutant Ala570Thr into a vector to obtain a recombinant vector; (see FIG. 6)

(2) transforming the recombinant vector described above into a host cell to obtain a recombinant expression cell clone;

(3) culturing the cell clone described above in a serum-free medium to express the mutein of the high-activity blood coagulation factor XI mutant Ala570Thr;

The serum-free medium is "SAFC Biosciences EX-CELL™ 302" (a commercial reagent). In order to ensure the safety of products and prevent blood-derived preparations from spreading infectious diseases, the serum-free medium was used for mammalian cell culture and protein expression. After the cells reached a steady state after logarithmic phase growth, the cell density was maintained within the target range and the high expression of the blood coagulation factor XI was maintained.

(4) separating, purifying and freeze-drying, so as to obtain the expressed blood coagulation factor XI mutein and related fusion protein.

After the medium was collected, the medium was clarified and filtered by a deep filter and further separated and purified. The purifying step was divided into two stages: primary purifying and refined purifying, wherein the primary purifying includes the following steps: the filtered and clarified culture solution was concentrated by 10-fold ultra-filtration, and lipid-enveloped viruses, i.e., HIV½, HCV, HBV, etc. were inactivated by an organic solvent/detergent method; and the refined purifying includes the following steps: the residual impurities, mainly other proteins secreted by the host cell were further removed from the product by chromatography such as ion exchange (an anion and a cation) and a molecular sieve. The purified protein was subjected to ultrafiltration, liquid exchange, formula adjustment, and then subjected to filtration with a 20 nm nano-membrane for virus removal and freeze-drying. The freeze-drying process includes quick freezing, quenching, freezing, vacuum, main drying and post-drying. The freeze-drying formula is based on inert sugars such as glycine, mannitol, sodium chloride, and calcium chloride, and inorganic salts (composed of glycine, mannitol, sodium chloride, calcium chloride, etc.; and the freeze-drying time is 30 h).

(5) Detection methods for the activity and antigen of the blood coagulation factor XI mutant Ala570Thr. The specific coagulation activity of the blood coagulation factor XI was calculated by comparing the coagulation activity of the blood coagulation factor XI measured by activated partial thromboplastin time (APTT) with the antigen measured by ELISA, as shown in FIG. 7. It can be seen from FIG. 7 that the blood coagulation factor XI mutant Ala570Thr has similar coagulation activity to the wild type.

Detection Methods for the Activity and Antigen of the Blood Coagulation Factor XI:

① Detection of the Activity of the Blood Coagulation Factor XI by a Coagulation Method:

Normal mixed plasma was diluted with OV Buffer at 1:10, 1:20, 1:40, 1:80, 1:160 and 1:320, respectively, and plasma samples to be tested were diluted at 1:10 and 1:20, and a cell supernatant was not treated. 50 μL of the diluted normal mixed plasma, the plasma sample to be tested or a cell supernatant transfected with a blood coagulation factor XI expression vector was taken, 50 μL of blood coagulation factor XI matrix plasma was added, an APTT reagent was added and the mixture was incubated for 3 minutes at 37° C. Then 50 μL of calcium chloride was added, and the coagulation time was recorded on an ST4 semi-automatic hemagglutinator (Stago, France). The activity of the blood coagulation factor XI of the normal mixed plasma diluted at 1:10 was 100%, and a standard curve was established based on the log values of the coagulation time and activity corresponding to different dilutions. If the correlation coefficient R2 is greater than 0.95, the value of the sample to be tested is brought into the calculation to obtain the activity of the blood coagulation factor XI of the sample to be tested.

② Detection of the Antigen of the Blood Coagulation Factor XI by a Double-Antibody Sandwich Method:

An antibody for coating (F9 ELISA kit, Affinity Biologicals, EIA9-0035R1) was diluted at 1:100 with a coating solution (1.59 g/L sodium carbonate and 2.94 g/L sodium bicarbonate, pH 9.6), and the diluted antibody was added at 100 μl/well, and incubated for 2 hours at room temperature. Washing was repeatedly performed for 3 times. Normal mixed plasma was subjected to two-fold dilution at 1:100 with a sample diluent (23.8 g HEPES (free acid)/L, 5.84 g/L NaCl, 3.72 g/L Na$_2$EDTA, 10 g/L BSA, 0.1% Tween-20, pH 7.2) to 1:3200, respectively. Plasma samples to be tested were diluted at 1:200, 1:400 and 1:800, and cell supernatants were a stock solution, and diluted at 1:10 and 1:100, respectively. 100 μl of the diluted normal mixed plasma or the sample to be tested was added to each well, and left at room temperature for 90 min. Washing was repeatedly performed for 3 times. The detection antibody was diluted with a sample diluent at 1:100, and 100 μl of the diluted detection antibody was added to each well, and left at room temperature for 90 min. Washing was repeatedly performed for 3 times. 100 μl of an OPD substrate was added to each well, and after a stable yellow color appeared (about 5-10 min), 100 μl of a stop solution was added to each well. An absorbance was read at a wavelength of 450 nm with a microplate reader. A standard curve was established, and the value for the antigen of the sample to be tested was calculated.

⑥ Correction of the Defects of Plasma Thrombin Generation in Hemophilia a Patients by the Blood Coagulation Factor XI Mutant A thrombin generation test (TGT) is a comprehensive test used to monitor the thrombin generation ability in plasma. An activator (including a tissue factor and phospholipid) was added into plasma to start a coagulation reaction, and then a thrombin-specific fluorescent substrate was added, and the generated thrombin catalyzed the substrate to release fluorescent groups. The generated fluorescent signal was monitored dynamically by a FLUOROSKAN fluorescence reader, and converted into a thrombin generation curve by using the matching thrombin generation experimental software. The thrombin generation ability was mainly evaluated by several parameters of the curve: (1) lag time, that is, the time required from the start of the reaction to the start of thrombin generation; (2) peak, that is, the maximum amount of generated thrombin; (3) time to peak (ttPeak), that is, the time required from the start of the reaction to the peak of thrombin; and (4) endogenous thrombin potential (ETP), that is, the area under the thrombin generation curve, reflecting the total amount of thrombin generation.

Figure 8:
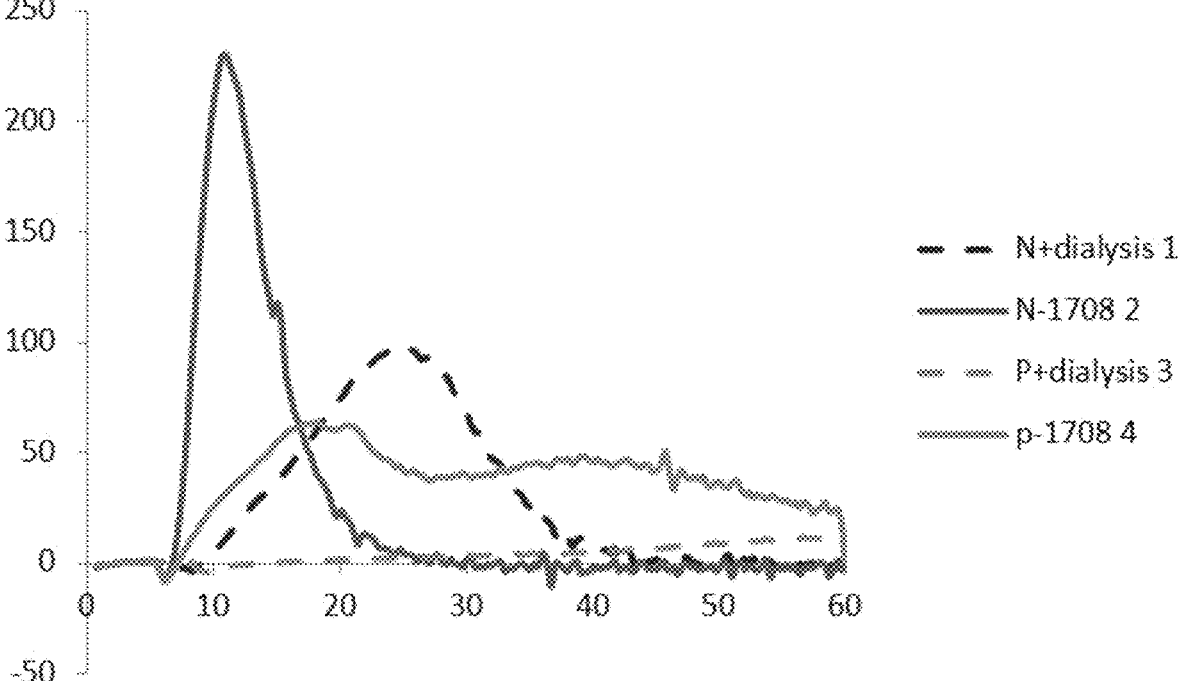
FIG. 8 is a schematic diagram showing correction of thrombin generation in platelet-rich plasma with blood coagulation factor VIII deficiency in vitro by the high-activity blood coagulation factor XI mutant Ala570Thr of the present invention.
Figure 9A:
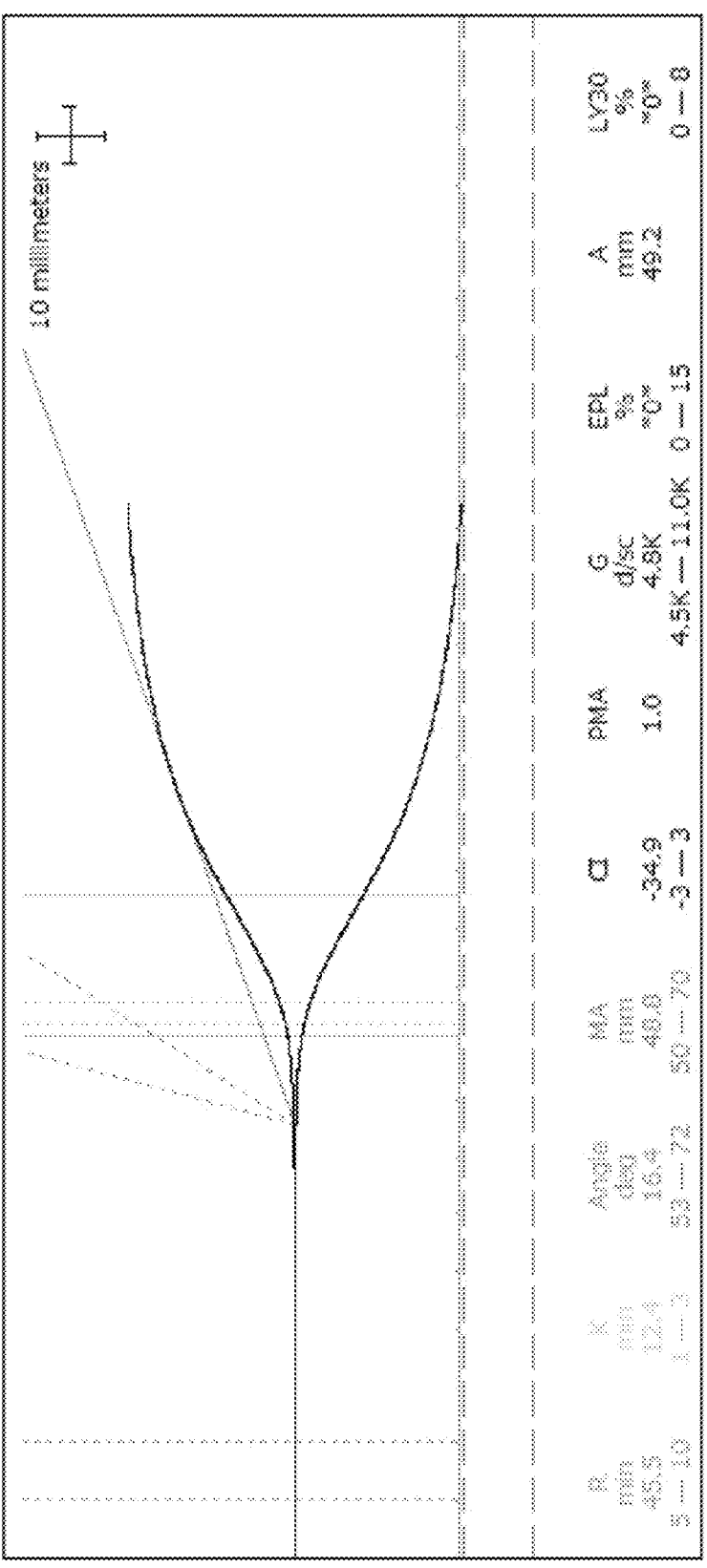
Figure 9B:
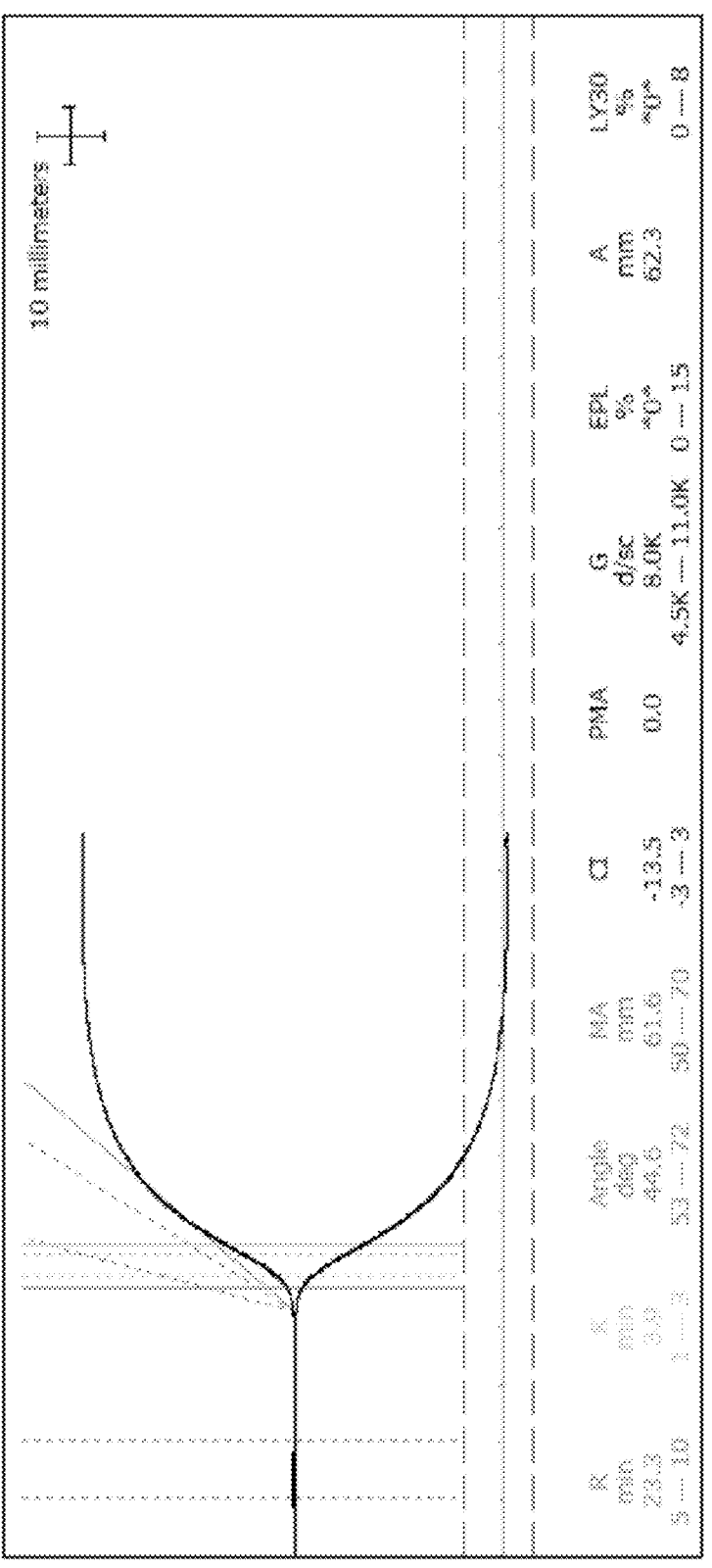
Figure 9C:
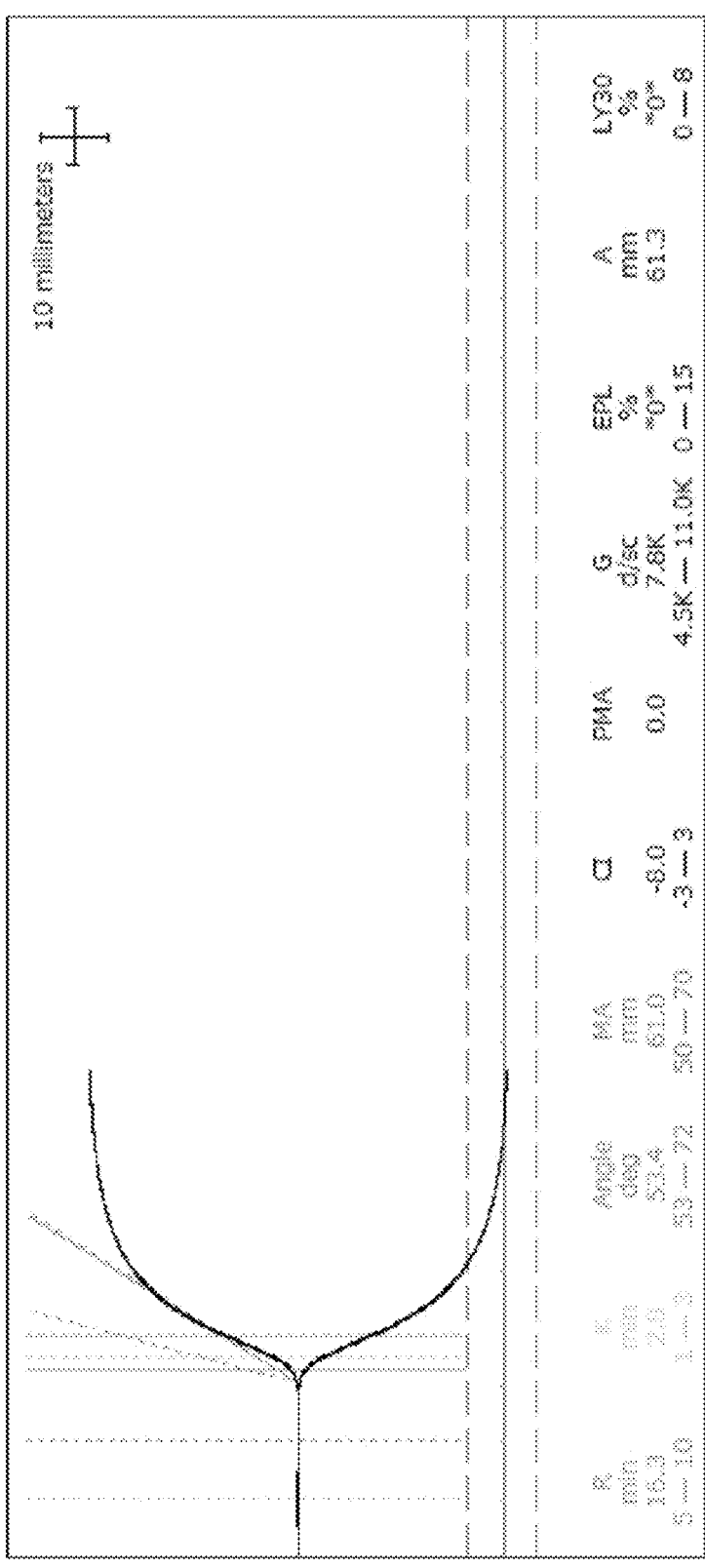
Figure 9D:
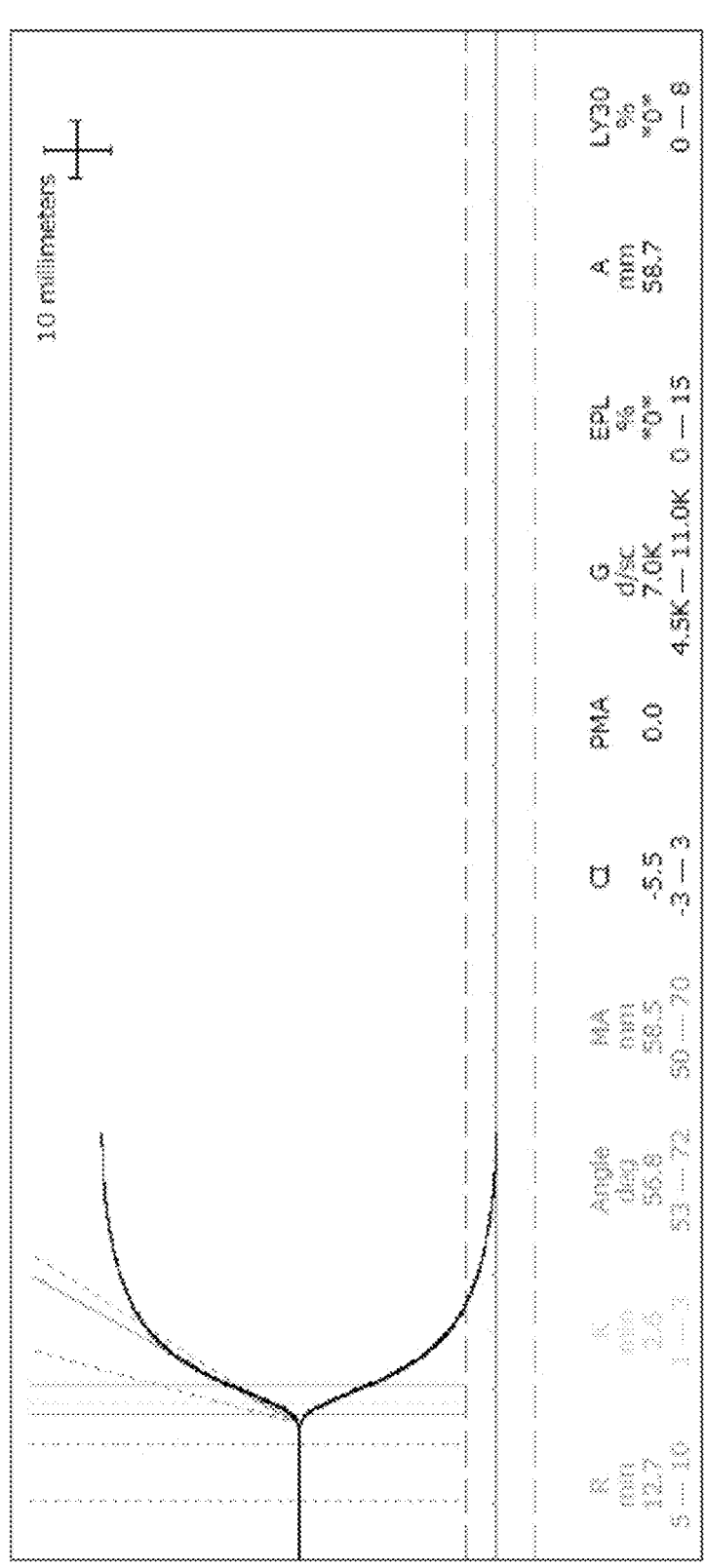
Figure 9E:
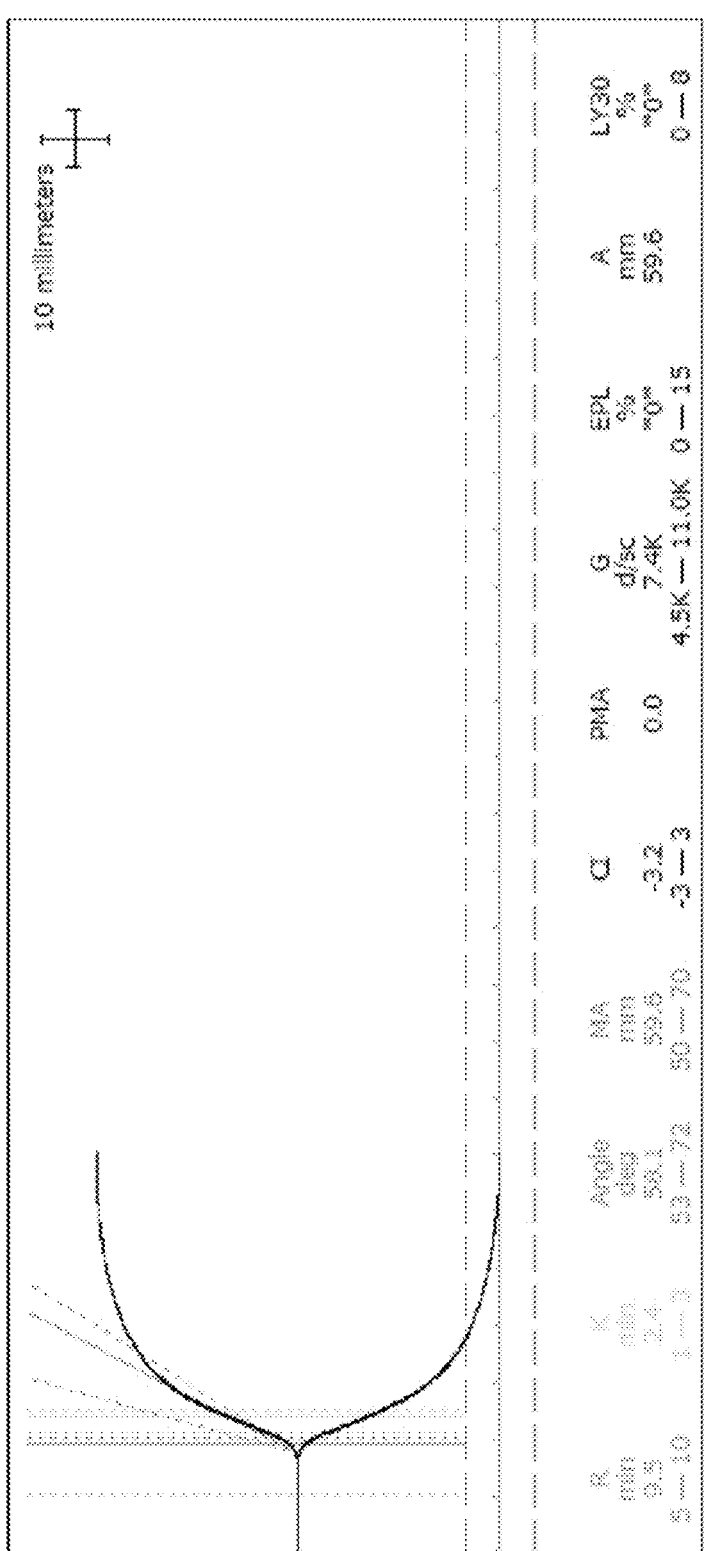
Figure 9F:
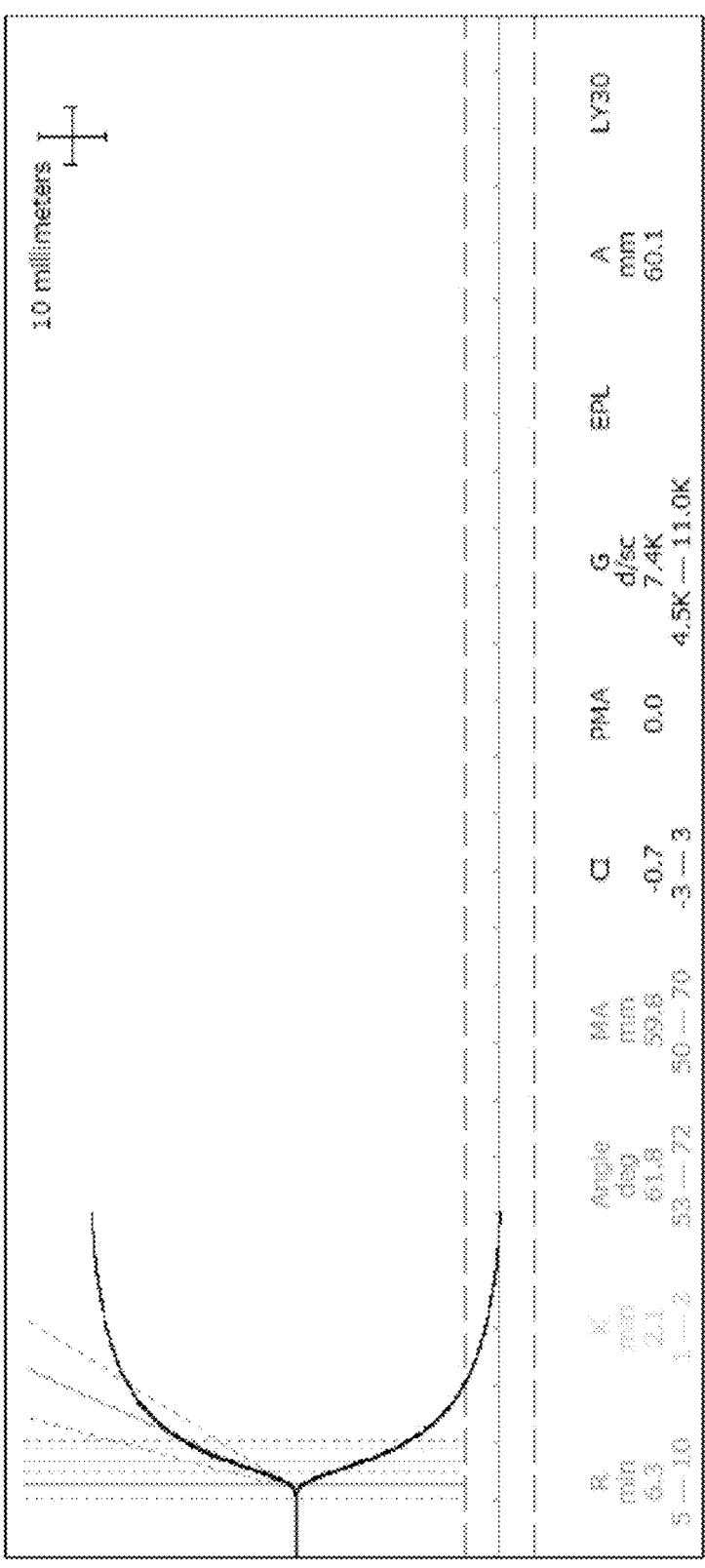
Figure 9G:
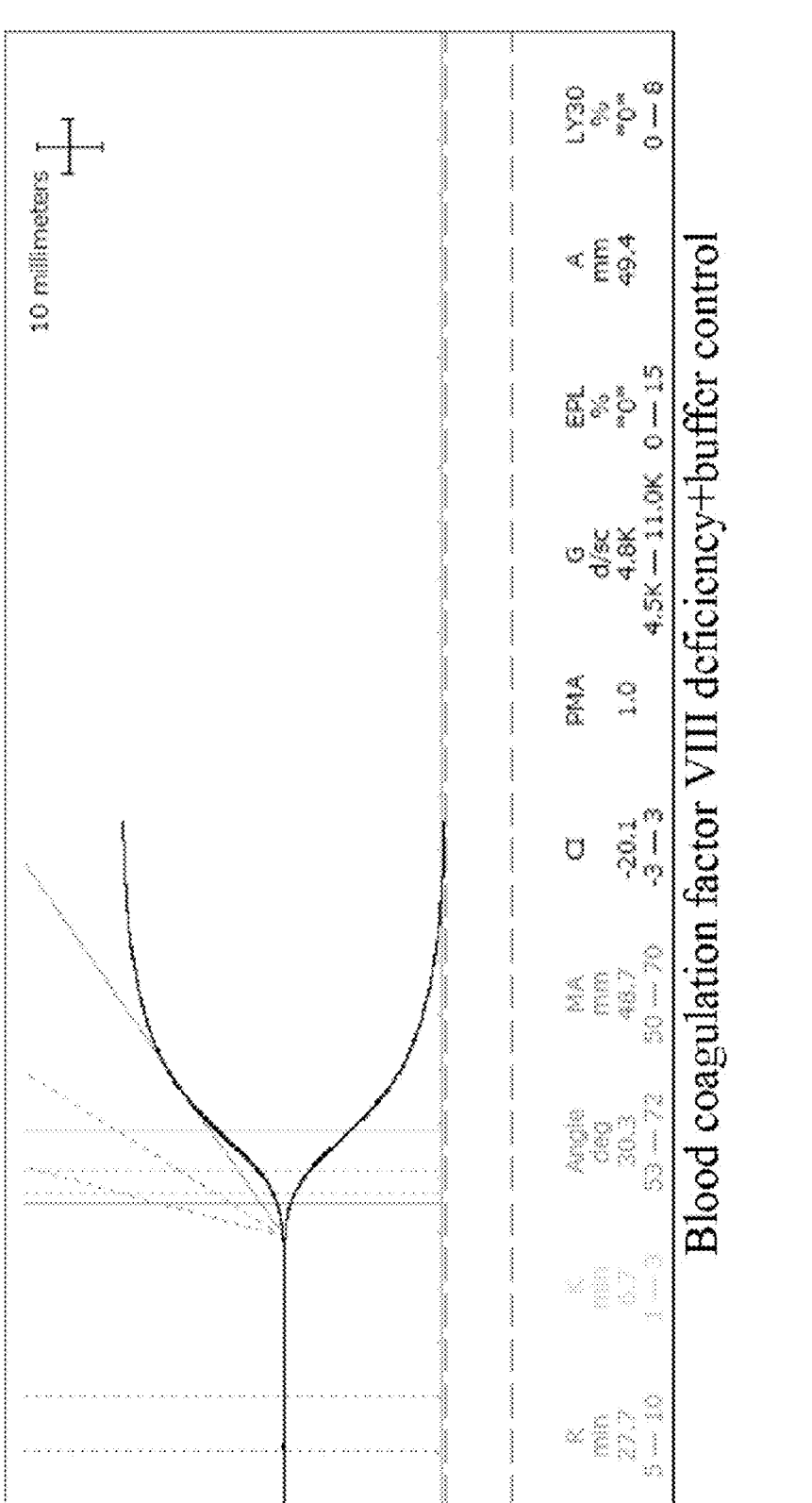
Figure 9H:
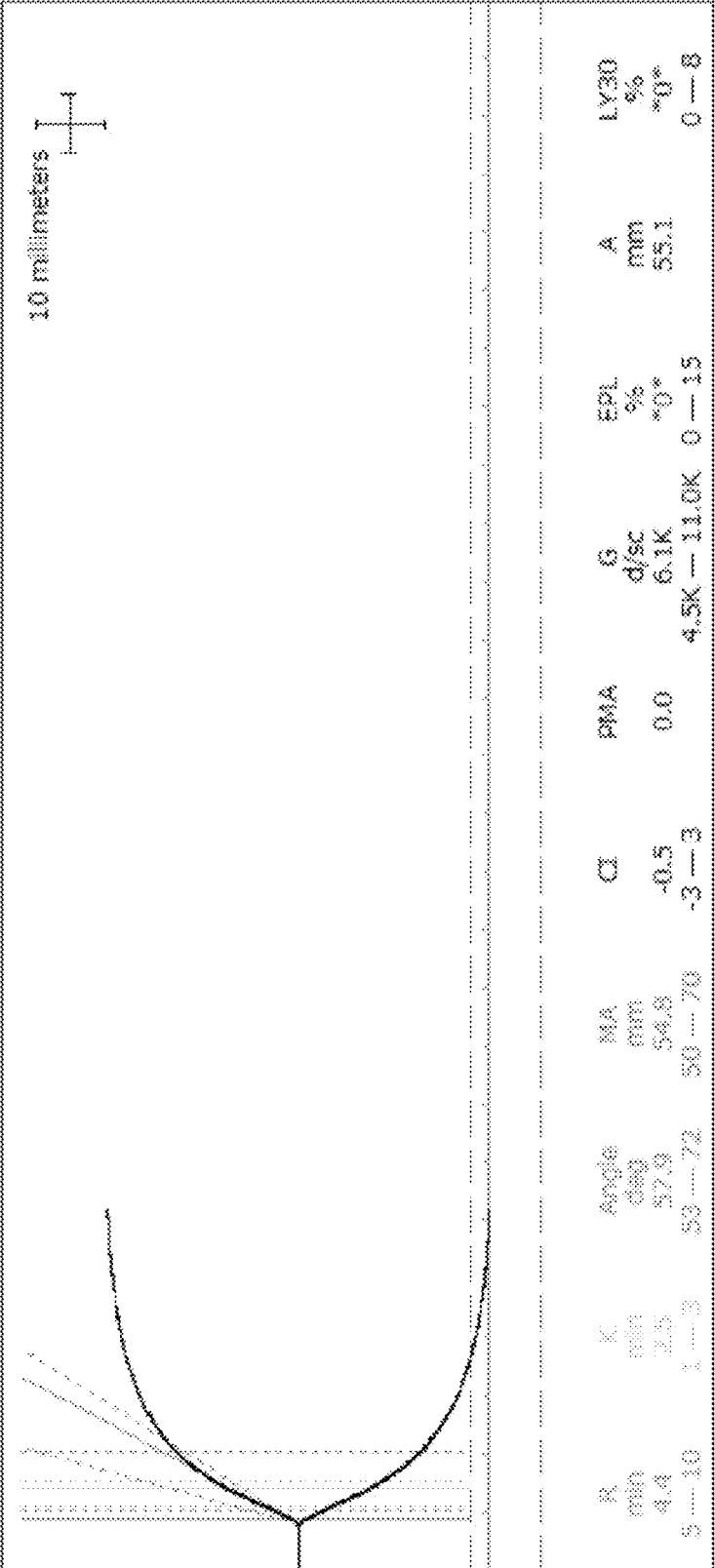

The thrombin generation test was performed by adding the blood coagulation factor XI mutant Ala570Thr (with the normal physiological concentration of 5 μg/mL) into a platelet-rich plasma (PRP) (deficiency of the coagulation factor VIII) from hemophilia A patients with antibodies (resisting the coagulation factor VIII), as shown in FIG. 8. FIG. 8 shows that the blood coagulation factor XI mutant Ala570Thr of the physiological concentration (5 μg/mL) can correct the thrombin generation disorder caused by blood coagulation factor VIII deficiency.

Embodiment 2

Detection of Thromboelastogram (See FIG. 9*a* to FIG. 9*h*)

Thromboelastogram (TEG) is a comprehensive test for monitoring the complete coagulation process in whole blood. Thromboelastogram does not require blood sample processing, and uses a small amount of whole blood to monitor the interactions between blood coagulation factors, platelets, fibrinogen, a fibrinolytic system and other cellular components, thus accurately providing a coagulation profile of patients. When testing, an anticoagulant was firstly added to an activation monitoring reagent bottle, and then a certain volume was sucked out and added to a special cylindrical cup (CaCl$_2$) was added in advance). The cup rotated at a constant speed at an angle of 4° 45' and a speed of 1 cycle/9 s, and the coagulation state of blood was monitored by a needle immersed in blood and suspended by a spiral wire, and a coagulation speed-intensity curve was drawn by a computer. The coagulation process was mainly evaluated by several parameters of the curve: (1) a R value for the reaction time, that is, the time required from the beginning of detection to the rise of curve amplitude to 2 mm, refers to the time required from the beginning of detection of a specimen to the beginning of fibrin clot formation; (2) a K value for the coagulation time and the clot formation rate α-angle, the K value for the coagulation time is the time required to record from the end of the coagulation time to the curve amplitude of 20 mm, and the clot formation rate α-angle refers to an angle between a tangent line made from the point of clot formation to a maximum arc of the thromboelastogram and a horizontal line, and the K value and the α-angle reflect the result of the joint action of fibrin and platelets at the beginning of blood clot formation, and are mainly influenced by the function of fibrinogen; (3) a MA value refers to a maximum amplitude on the thromboelastogram, that is, the maximum shear force coefficient. The MA value reflects the strongest dynamic characteristics of the interaction between fibrin being formed and platelets and the stability of blood clot formation, where the role of platelets is greater than that of fibrinogen, accounting for about 80%; and (4) a comprehensive coagulation index, i.e., a CI value, is calculated by combining the reaction time, coagulation time, clot formation rate and maximum amplitude of the thromboelastogram curve. The CI value reflects the comprehensive coagulation status of the sample under various conditions, which indicates the presence of low coagulation when the CI value is less than −3, the presence of high coagulation when the CI value is higher than 3, and the presence of normal coagulation when the CI value is −3 to 3.

It can be seen from FIG. 9*a* to FIG. 9*h* that the blood coagulation factor XI mutant Ala570Thr can correct the coagulation defects caused by coagulation factor VIII deficiency and the presence of antibodies to the coagulation factor VIII.

What is claimed is:

1. A blood coagulation factor XI mutant Ala570Thr nucleic acid sequence, having:

(a) the nucleotide sequence as shown in SEQ ID NO: 1; or (b) the nucleotide sequence as shown in SEQ ID NO: 2; or (c) the nucleotide sequence as shown in SEQ ID NO: 3; or (d) the nucleotide sequence as shown in SEQ ID NO: 4.

2. A method for preparing a mutant of a blood coagulation factor XI mutant Ala570Thr, comprising the following steps:

(a) ligating a nucleic acid sequence encoding the blood coagulation factor XI mutant Ala570Thr according to claim 1 into a vector to obtain a recombinant vector;

(b) transforming the recombinant vector above of step (a) into a host cell to obtain clones of mutant cells expressing a recombinant blood coagulation factor XI mutant Ala570Thr;

(c) performing continuous perfusion culture on the clones of mutant cells in a serum-free medium to induce expression of the mutant of the recombinant blood coagulation factor XI mutant Ala570Thr; and (d) separating, purifying, filtering, and freeze-drying to obtain the expressed blood coagulation factor XI mutant Ala570Thr mutant.

3. A blood coagulation factor XI mutant Ala570Thr, comprising the amino acid sequence of SEQ ID NO: 5, and an amino acid located at position 570 of the mutant is Thr rather than Ala of non-human wild-type factor XI.

4. A nucleic acid encoding the mutant according to claim 3, or a nucleic acid having the same length as the coding nucleic acid and being completely complementary to the coding nucleic acid.

5. A vector expressing the mutant according to claim 3.

* * * * *

SEQUENCE LISTING

```
<160> NUMBER OF SEQ ID NOS: 5

<210> SEQ ID NO 1
<211> LENGTH: 1878
<212> TYPE: DNA
<213> ORGANISM: Artificial Sequence
<220> FEATURE:
<223> OTHER INFORMATION: Synthesized

<400> SEQUENCE: 1
tgattttctt atatcaagtg gtacatttca ttttatttac ttcagtttct ggtgaatgtg        60
tgactcagtt gttgaaggac acctgctttg aaggagggga cattactacg gtcttcacac       120
caagcgccaa gtactgccag gtagtctgca cttaccaccc aagatgttta ctcttcactt       180
tcacggcgga atcaccatct gaggatccca cccgatggtt tacttgtgtc ctgaaagaca       240
gtgttacaga aacactgcca agagtgaata ggacagcagc gatttctggg tattctttca       300
agcaatgctc acaccaaata agcgcttgca acaaagacat ttatgtggac ctagacatga       360
agggcataaa ctataacagc tcagttgcca agagtgctca agaatgccaa gaaagatgca       420
cggatgacgt ccactgccac tttttcacgt acgccacaag gcagtttccc agcctggagc       480
atcgtaacat ttgtctactg aagcacaccc aaacagggac accaaccaga ataacgaagc       540
tcgataaagt ggtgtctgga ttttcactga aatcctgtgc actttctaat ctggcttgta       600
ttagggacat tttccctaat acggtgtttg cagacagcaa catcgacagt gtcatggctc       660
ccgatgcttt tgtctgtggc cgaatctgca ctcatcatcc cggttgcttg ttttttacct       720
tcttttccca ggaatggccc aaagaatctc aaagaaatct ttgtctcctt aaaacatctg       780
agagtggatt gcccagtaca cgcattaaaa agagcaaagc tctttctggt ttcagtctac       840
aaagctgcag gcacagcatc ccagtgttct gccattcttc attttaccat gacactgatt       900
```

```
tcttgggaga agaactggat attgttgctg caaaaagtca cgaggcctgc cagaaactgt      960
gcaccaatgc cgtccgctgc cagttttttta cctataccccc agcccaagca tcctgcaacg     1020
aagggaaggg caagtgttac ttaaagcttt cttcaaacgg atctccaact aaaatacttc     1080
acgggagagg aggcatctct ggatacacat taaggttgtg taaaatggat aatgagtgta     1140
ccaccaaaat caagcccagg atcgttggag gaactgcgtc tgttcgtggt gagtggccgt     1200
ggcaggtgac cctgcacaca acctcaccca ctcagagaca cctgtgtgga ggctccatca     1260
ttggaaacca gtggatatta acagccgctc actgtttcta tggggtagag tcacctaaga     1320
ttttgcgtgt ctacagtggc attttaaatc aatctgaaat aaaagaggac acatctttct     1380
ttggggttca agaaataata atccatgatc agtataaaat ggcagaaagc gggtatgata     1440
ttgccttgtt gaaactggaa accacagtga attacacaga ttctcaacga cccatatgcc     1500
tgccttccaa aggagataga aatgtaatat acactgattg ctgggtgact ggatgggggt     1560
acagaaaact aagagacaaa atacaaaata ctctccagaa agccaagata cccttagtga     1620
ccaacgaaga gtgccagaag agatacagag gacataaaat aacccataag atgatctgtg     1680
ccggctacag ggaaggaggg aaggacactt gcaagggaga ttcgggaggc cctctgtcct     1740
gcaaacacaa tgaggtctgg catctggtag gcatcacgag ctggggcgaa ggctgtgctc     1800
aaagggagcg gccaggtgtt tacaccaacg tggtcgagta cgtggactgg attctggaga     1860
aaaactcaag cagtgtga                                                   1878

<210> SEQ ID NO 2
<211> LENGTH: 1878
<212> TYPE: DNA
<213> ORGANISM: Artificial Sequence
<220> FEATURE:
<223> OTHER INFORMATION: Synthesized

<400> SEQUENCE: 2 tgatttctt atatcaagtg gtacatttca ttttatttac ttcagtttct ggtgaatgtg       60
tgactcagtt gttgaaggac acctgctttg aaggagggga cattactacg gtcttcacac      120
caagcgccaa gtactgccag gtagtctgca cttaccaccc aagatgttta ctcttcactt      180
tcacggcgga atcaccatct gaggatccca cccgatggtt tacttgtgtc ctgaaagaca      240
gtgttacaga aacactgcca agagtgaata ggacagcagc gatttctggg tattctttca      300
agcaatgctc acaccaaata agcgcttgca acaaagacat ttatgtggac ctagacatga      360
agggcataaa ctataacagc tcagttgcca agagtgctca agaatgccaa gaaagatgca      420
cggatgacgt ccactgccac ttttttcacgt acgccacaag gcagtttccc agcctggagc      480
atcgtaacat ttgtctactg aagcacaccc aaacagggac accaaccaga ataacgaagc      540
tcgataaagt ggtgtctgga ttttcactga atcctgtgc actttctaat ctggcttgta      600
ttagggacat tttccctaat acggtgtttg cagacagcaa catcgacagt gtcatggctc      660
ccgatgcttt tgtctgtggc cgaatctgca ctcatcatcc cggttgcttg tttttttacct     720 tcttttccca ggaatggccc aaagaatctc aaagaaatct ttgtctcctt aaaacatctg      780
agagtggatt gcccagtaca cgcattaaaa agagcaaagc tctttctggt ttcagtctac      840
aaagctgcag gcacagcatc ccagtgttct gccattcttc attttaccat gacactgatt      900
tcttgggaga agaactggat attgttgctg caaaaagtca cgaggcctgc cagaaactgt      960
gcaccaatgc cgtccgctgc cagttttttta cctataccccc agcccaagca tcctgcaacg     1020
aagggaaggg caagtgttac ttaaagcttt cttcaaacgg atctccaact aaaatacttc     1080
```

-continued

```
acgggagagg aggcatctct ggatacacat taaggttgtg taaaatggat aatgagtgta      1140
ccaccaaaat caagcccagg atcgttggag gaactgcgtc tgttcgtggt gagtggccgt      1200
ggcaggtgac cctgcacaca acctcaccca ctcagagaca cctgtgtgga ggctccatca      1260
ttggaaacca gtggatatta acagccgctc actgtttcta tggggtagag tcacctaaga      1320
ttttgcgtgt ctacagtggc attttaaatc aatctgaaat aaaagaggac acatctttct      1380
ttggggttca agaaataata atccatgatc agtataaaat ggcagaaagc gggtatgata      1440
ttgccttgtt gaaactggaa accacagtga attacacaga ttctcaacga cccatatgcc      1500
tgccttccaa aggagataga aatgtaatat acactgattg ctgggtgact ggatggggggt      1560 acagaaaact aagagacaaa atacaaaata ctctccagaa agccaagata cccttagtga      1620
ccaacgaaga gtgccagaag agatacagag gacataaaat aacccataag atgatctgtg      1680
ccggctacag ggaaggaggg aaggacacct gcaagggaga ttcgggaggc cctctgtcct      1740
gcaaacacaa tgaggtctgg catctggtag gcatcacgag ctggggcgaa ggctgtgctc      1800
aaagggagcg gccaggtgtt tacaccaacg tggtcgagta cgtggactgg attctggaga      1860
aaaactcaag cagtgtga                                                    1878
```

<210> SEQ ID NO 3
<211> LENGTH: 1878
<212> TYPE: DNA
<213> ORGANISM: Artificial Sequence
<220> FEATURE:
<223> OTHER INFORMATION: Synthesized

<400> SEQUENCE: 3

```
tgattttctt atatcaagtg gtacatttca ttttatttac ttcagtttct ggtgaatgtg        60
tgactcagtt gttgaaggac acctgctttg aaggagggga cattactacg gtcttcacac       120
caagcgccaa gtactgccag gtagtctgca cttaccaccc aagatgttta ctcttcactt       180
tcacggcgga atcaccatct gaggatccca cccgatggtt tacttgtgtc ctgaaagaca       240
gtgttacaga aacactgcca agagtgaata ggacagcagc gatttctggg tattctttca       300
agcaatgctc acaccaaata agcgcttgca acaaagacat ttatgtggac ctagacatga       360
agggcataaa ctataacagc tcagttgcca agagtgctca agaatgccaa gaaagatgca       420
cggatgacgt ccactgccac ttttttcacgt acgccacaag gcagtttccc agcctggagc       480
atcgtaacat ttgtctactg aagcacaccc aaacagggac accaaccaga ataacgaagc       540
tcgataaagt ggtgtctgga ttttcactga atcctgtgc actttctaat ctggcttgta       600
ttagggacat tttccctaat acggtgtttg cagacagcaa catcgacagt gtcatggctc       660
ccgatgcttt tgtctgtggc cgaatctgca ctcatcatcc cggttgcttg ttttttacct       720
tcttttccca ggaatggccc aaagaatctc aaagaaatct ttgtctcctt aaaacatctg       780
agagtggatt gcccagtaca cgcattaaaa agagcaaagc tctttctggt ttcagtctac       840
aaagctgcag gcacagcatc ccagtgttct gccattcttc attttaccat gacactgatt       900
tcttgggaga agaactggat attgttgctg caaaaagtca cgaggcctgc cagaaactgt       960
gcaccaatgc cgtccgctgc cagttttttta cctatacccc agcccaagca tcctgcaacg      1020
aagggaaggg caagtgttac ttaaagcttt cttcaaacgg atctccaact aaaatacttc      1080
acgggagagg aggcatctct ggatacacat taaggttgtg taaaatggat aatgagtgta      1140
ccaccaaaat caagcccagg atcgttggag gaactgcgtc tgttcgtggt gagtggccgt      1200
```

```
ggcaggtgac cctgcacaca acctcaccca ctcagagaca cctgtgtgga ggctccatca    1260
ttggaaacca gtggatatta acagccgctc actgtttcta tggggtagag tcacctaaga    1320
ttttgcgtgt ctacagtggc attttaaatc aatctgaaat aaaagaggac acatctttct    1380 ttgggggttca agaaataata atccatgatc agtataaaat ggcagaaagc gggtatgata    1440
ttgccttgtt gaaactggaa accacagtga attacacaga ttctcaacga cccatatgcc    1500
tgccttccaa aggagataga aatgtaatat acactgattg ctgggtgact ggatggggt     1560 acagaaaact aagagacaaa atacaaaata ctctccagaa agccaagata cccttagtga    1620
ccaacgaaga gtgccagaag agatacagag gacataaaat aacccataag atgatctgtg    1680
ccggctacag ggaaggaggg aaggacacgt gcaagggaga ttcgggaggc cctctgtcct    1740
gcaaacacaa tgaggtctgg catctggtag gcatcacgag ctggggcgaa ggctgtgctc    1800
aaagggagcg gccaggtgtt tacaccaacg tggtcgagta cgtggactgg attctggaga    1860
aaaactcaag cagtgtga                                                    1878
```

<210> SEQ ID NO 4
<211> LENGTH: 1878
<212> TYPE: DNA
<213> ORGANISM: Artificial Sequence
<220> FEATURE:
<223> OTHER INFORMATION: Synthesized

<400> SEQUENCE: 4

```
tgattttctt atatcaagtg gtacatttca ttttatttac ttcagtttct ggtgaatgtg      60
tgactcagtt gttgaaggac acctgctttg aaggagggga cattactacg gtcttcacac     120
caagcgccaa gtactgccag gtagtctgca cttaccaccc aagatgttta ctcttcactt     180
tcacggcgga atcaccatct gaggatccca cccgatggtt tacttgtgtc ctgaaagaca     240
gtgttacaga aacactgcca agagtgaata ggacagcagc gatttctggg tattctttca     300
agcaatgctc acaccaaata agcgcttgca acaaagacat ttatgtggac ctagacatga     360
agggcataaa ctataacagc tcagttgcca agagtgctca agaatgccaa gaaagatgca     420
cggatgacgt ccactgccac tttttcacgt acgccacaag gcagtttccc agcctggagc     480
atcgtaacat ttgtctactg aagcacaccc aaacagggac accaaccaga ataacgaagc     540
tcgataaagt ggtgtctgga ttttcactga atcctgtgc actttctaat ctggcttgta      600
ttagggacat tttccctaat acggtgtttg cagacagcaa catcgacagt gtcatggctc     660
ccgatgcttt tgtctgtggc cgaatctgca ctcatcatcc cggttgcttg ttttttacct     720
tcttttccca ggaatggccc aaagaatctc aaagaaatct ttgtctcctt aaaacatctg     780
agagtggatt gcccagtaca cgcattaaaa agagcaaagc tctttctggt ttcagtctac     840
aaagctgcag gcacagcatc ccagtgttct gccattcttc attttaccat gacactgatt     900
tcttgggaga agaactggat attgttgctg caaaaagtca cgaggcctgc cagaaactgt     960
gcaccaatgc cgtccgctgc cagttttttta cctatacccc agcccaagca tcctgcaacg    1020
aagggaaggg caagtgttac ttaaagcttt cttcaaacgg atctccaact aaaatacttc    1080 acggagagg aggcatctct ggatacacat taaggttgtg taaaatggat aatgagtgta     1140
ccaccaaaat caagcccagg atcgttggag gaactgcgtc tgttcgtggt gagtggccgt    1200
ggcaggtgac cctgcacaca acctcaccca ctcagagaca cctgtgtgga ggctccatca    1260
ttggaaacca gtggatatta acagccgctc actgtttcta tggggtagag tcacctaaga    1320
ttttgcgtgt ctacagtggc attttaaatc aatctgaaat aaaagaggac acatctttct    1380
```

-continued

```
ttggggttca agaaataata atccatgatc agtataaaat ggcagaaagc gggtatgata    1440
ttgccttgtt gaaactggaa accacagtga attacacaga ttctcaacga cccatatgcc    1500
tgccttccaa aggagataga aatgtaatat acactgattg ctgggtgact ggatgggggt    1560
acagaaaact aagagacaaa atacaaaata ctctccagaa agccaagata cccttagtga    1620
ccaacgaaga gtgccagaag agatacagag gacataaaat aacccataag atgatctgtg    1680
ccggctacag ggaaggaggg aaggacacat gcaaggggag ttcgggaggc cctctgtcct    1740
gcaaacacaa tgaggtctgg catctggtag gcatcacgag ctggggcgaa ggctgtgctc    1800
aaagggagcg gccaggtgtt tacaccaacg tggtcgagta cgtggactgg attctggaga    1860
aaaactcaag cagtgtga                                                  1878
```

<210> SEQ ID NO 5
<211> LENGTH: 625
<212> TYPE: PRT
<213> ORGANISM: Artificial Sequence
<220> FEATURE:
<223> OTHER INFORMATION: Synthesized

<400> SEQUENCE: 5

```
Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
        35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
                85                  90                  95

Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
    130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
            195                 200                 205

Val Phe Ala Asp Ser Asn Ile Asp Ser Val Met Ala Pro Asp Ala Phe
        210                 215                 220

Val Cys Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
            260                 265                 270
```

-continued

```
Lys Ala Leu Ser Gly Phe Ser Leu Gln Ser Cys Arg His Ser Ile Pro
    275                 280                 285

Val Phe Cys His Ser Ser Phe Tyr His Asp Thr Asp Phe Leu Gly Glu
    290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
                340                 345                 350

Asn Gly Ser Pro Thr Lys Ile Leu His Gly Arg Gly Gly Ile Ser Gly
                355                 360                 365

Tyr Thr Leu Arg Leu Cys Lys Met Asp Asn Glu Cys Thr Thr Lys Ile
    370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
                420                 425                 430

Phe Tyr Gly Val Glu Ser Pro Lys Ile Leu Arg Val Tyr Ser Gly Ile
                435                 440                 445

Leu Asn Gln Ser Glu Ile Lys Glu Asp Thr Ser Phe Phe Gly Val Gln
    450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
                500                 505                 510

Asp Cys Trp Val Thr Gly Trp Gly Tyr Arg Lys Leu Arg Asp Lys Ile
                515                 520                 525

Gln Asn Thr Leu Gln Lys Ala Lys Ile Pro Leu Val Thr Asn Glu Glu
    530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Thr Cys Lys Gly Asp Ser Gly
                565                 570                 575

Gly Pro Leu Ser Cys Lys His Asn Glu Val Trp His Leu Val Gly Ile
                580                 585                 590

Thr Ser Trp Gly Glu Gly Cys Ala Gln Arg Glu Arg Pro Gly Val Tyr
                595                 600                 605

Thr Asn Val Val Glu Tyr Val Asp Trp Ile Leu Glu Lys Thr Gln Ala
    610                 615                 620

Val
625
```